US012690939B2

(12) United States Patent
Deboeck et al.

(10) Patent No.: US 12,690,939 B2
(45) Date of Patent: ***Jul. 28, 2026

(54) MEDICAL FIXATION DEVICE FOR CONNECTING SURGICAL INSTRUMENTS TO AN OPERATING TABLE

(71) Applicant: MEDENVISION, Westerlo (BE)

(72) Inventors: Pieter Deboeck, Tielt-Winge (BE);
Filip Van Limbergen, Hulshout (BE);
Wouter Foulon, Lubbeek (BE);
Kristoff Corten, Wolfsdonk (BE);
Floris Goyens, Antwerp (BE)

(73) Assignee: Medenvision, Westerlo (BE)

( * ) Notice: Subject to any disclaimer, the term of this patent is extended or adjusted under 35 U.S.C. 154(b) by 13 days.

This patent is subject to a terminal disclaimer.

(21) Appl. No.: 18/439,498

(22) Filed: Feb. 12, 2024

(65) Prior Publication Data

US 2025/0082431 A1     Mar. 13, 2025

(30) Foreign Application Priority Data

Sep. 13, 2023   (BE) .................................... 2023/5748
Feb. 9, 2024   (BE) .................................... 2024/5088

(51) Int. Cl.
*A61B 90/57*     (2016.01)
*A61B 17/02*     (2006.01)
*A61B 17/00*     (2006.01)

(52) U.S. Cl.
CPC .......... *A61B 90/57* (2016.02); *A61B 17/0206* (2013.01); *A61B 2017/00477* (2013.01); *A61B 2090/571* (2016.02)

(58) Field of Classification Search
CPC ..... A61B 17/00; A61B 17/02; A61B 17/0206; A61B 90/57; A61B 2017/00477; A61B 2090/571
See application file for complete search history.

(56) References Cited

U.S. PATENT DOCUMENTS

| | | | |
|---|---|---|---|
| 4,143,652 A | 3/1979 | Meier et al. | |
| 5,704,900 A | 1/1998 | Dobrovolny et al. | |
| 6,209,835 B1 * | 4/2001 | Walrath ................ | F16M 11/28 |
| | | | 248/276.1 |
| 2011/0253653 A1 | 10/2011 | Chang | |
| 2013/0023735 A1 | 1/2013 | Brown et al. | |
| 2013/0123911 A1 | 5/2013 | Chalekian et al. | |
| 2022/0031399 A1 * | 2/2022 | Azulay ................ | A61B 34/30 |

OTHER PUBLICATIONS

Beligum Search Report, Mar. 8, 2024.

* cited by examiner

*Primary Examiner* — Vi X Nguyen
(74) *Attorney, Agent, or Firm* — Rutan & Tucker LLP; Hani Z. Sayed

(57) ABSTRACT
The present invention relates to medical devices and medical device systems for keeping open a wound during surgery as well as to devices and systems for assisting in positioning and keeping in place biological tissue during surgery. More particularly, the present invention relates to medical fixation devices for connecting surgical instruments, such as surgical retractors, to an operating table, as well as medical device sets and medical device systems comprising such medical fixation devices. In addition, the present invention relates to methods for installation of such medical fixation devices, medical device sets and medical device systems.

20 Claims, 18 Drawing Sheets

MEDICAL FIXATION DEVICE FOR CONNECTING SURGICAL INSTRUMENTS TO AN OPERATING TABLE

PRIORITY

This application claims the benefit of and priority to Belgian Patent Application No. BE2023/5748, filed on Sep. 13, 2023 and Belgian Patent Application No. BE2024/5088, filed on Feb. 9, 2024, the entirety of said applications being incorporated herein by reference.

FIELD OF THE INVENTION

The present invention relates to medical devices and medical device systems for keeping open a wound during surgery as well as to devices and systems for assisting in positioning and keeping in place biological tissue during surgery. More particularly, the present invention relates to medical fixation devices for connecting surgical instruments, such as surgical retractors, to an operating table, as well as medical device sets and medical device systems comprising such medical fixation devices. In addition, the present invention relates to methods for installation of such medical fixation devices, medical device sets and medical device systems.

BACKGROUND OF THE INVENTION

During open surgery, the incision through which surgical procedures are to be performed needs to be expanded and kept open in order to provide to the surgeon sufficient view and access to the surgical site for performing the procedure. Typically, surgical retractors are used for this, i.e. elements for expanding the edges of the incision for keeping the wound open. During surgery, typically supporting staff of the surgeon assist by handling the surgical retractors for expanding the incision to keep the wound open. However, this requires a lot of personnel, and is costly and inefficient. Furthermore, it's difficult to keep the retractors at a fixed and stable position, due to for example fatigue, loss of focus or distraction of an assistant (human retractor holder).

Some surgical retracting systems are known wherein the surgical retractors can be connected to external fixation devices, which can in turn be connected to the patient or to the operating table, instead of being manually held by the personnel. For example, patent application WO 2013/092938 A1 describes a surgical retracting system wherein the surgical retractors comprise or are coupled to a mechanical retracting system, which can be connected to an external fixation device. In the orthopedic field, such solutions are often specifically designed for hip, knee or spine surgery.

Various other surgeries require connection of surgical retractors to external fixation devices in the space around the operating table. For example, this is the case for shoulder surgeries performed in beach chair position, whereby the patient is in a sitting or a semi-sitting surgical position, and the surgical retractors need to be connected in the space around the patient's shoulder. To date, external medical fixation devices for connection of surgical retractors in the space around the operating table do not exist in the field of shoulder surgery.

Some devices are known for positioning and fixation of the patient's body parts, in the space around the operating table during surgery. TRIMANO® Support Arm is an external fixation device for holding the patient's arm in a desired position during shoulder surgery performed in the beach chair position. This device comprises several mechanical elements which can be moved with respect to each other, and a clamping means for fixation onto an operating table. WO 01/45601 A2 describes a device for distraction and positioning of the ankle in the space around the operating table for ankle surgery. This device comprises a distractor arm with a connector loop for foot strap, a lever arm, and a clamping means for angular positioning and fixation with respect to an operating table.

However, these devices are not suitable for connection of surgical retractors in the space around the operating table. TRIMANO® Support Arm is complex, expensive, and comprises no means for connection of surgical retractors. The ankle distraction and positioning device from WO 01/45601 A2 is simpler and could theoretically be connected to one surgical retractor by the connector loop. However, the connections between the different elements of this device are not sufficiently robust to avoid wiggling of the entire device each time surgical retractors are being connected, disconnected or repositioned. Furthermore, it is time-consuming to set up the ankle distraction and positioning device for an individual patient and surgery.

Thus, there is a need for an improved external fixation device, which enables fast and easy connection of surgical retractors and other surgical instruments to an operating table in the space around the operating table, and which is sufficiently robust to maintain its position when forces are exerted thereon by the surgical retractors.

SUMMARY OF THE INVENTION

In a first aspect, the present invention concerns a medical fixation device for connecting one or more surgical instruments such as retractor devices to an operating table in the space around the operating table, the medical fixation device comprising:

- two elongate elements, a first elongate element and a second elongate element,
- a connection part for connecting the first elongate element to the second elongate element,
- a means for secure fixation of the first elongate element in at least one fixed angular position relative to the second elongate element,
- a base element connected to the second elongate element and configured to be connected to the operating table,
- a means for secure fixation of the second elongate element to the base element, and
- a means for secure fixation of the base element to the operating table,
- wherein the first elongate element is configured to be releasably connected to one or more, preferably two or more, more preferably three or more, surgical instruments, wherein the connection part is configured to allow rotatable connection of the first elongate element relative to the second elongate element when the means for the secure fixation is not connected, and wherein the connection part is configured to enable secure fixation of the first elongate in at least one fixed angular position relative to the second elongate element when the means for the secure fixation is connected.

In another aspect, the present invention concerns a medical fixation device for connecting one or more surgical instruments such as retractor devices to an operating table in the space around the operating table, the medical device comprising:

two elongate elements, a first elongate element and a second elongate element, wherein an end of the first elongate element is connected to an end of the second elongate element, a means for secure fixation of the first elongate element in at least one fixed angular position relative to the second elongate element, a base element connected to the second elongate element and configured to be connected to the operating table, a means for secure fixation of the second elongate element to the base element, and a means for secure fixation of the base element to the operating table, wherein the first elongate element is configured to be releasably connected to one or more, preferably two or more, more preferably three or more, surgical instruments, and wherein the connection between the first elongate element and the second elongate element is configured to allow rotatable connection of the first elongate element relative to the second elongate element when the means for secure fixation of the first elongate element in the at least one fixed angular position relative to the second elongate element is not connected.

In another aspect, the present invention concerns a medical fixation device for connecting one or more retractor devices to an operating table in the space around the operating table, the medical fixation device comprising:

two elongate elements, a first elongate element and a second elongate element, wherein an end of the first elongate element is connected to an end of the second elongate element, a means for secure fixation of the first elongate element in at least one fixed angular position relative to the second elongate element;

a base element releasably connected to the second elongate element and configured to be connected to the operating table, a means for secure fixation of the second elongate element to the base element, and a means for secure fixation of the base element to the operating table, wherein the first elongate element is configured to be releasably connected to two or more retractor devices, and wherein the connection between the first elongate element and the second elongate element is configured to allow rotatable connection of the first elongate element relative to the second elongate element when the secure fixation of the first elongate element in the at least one fixed angular position relative to the second elongate element is not connected.

It is an advantage of the medical fixation device according to the invention that it enables connection of surgical instruments, such as surgical retractors, to an operating table in the space around the operating table. The space around the operating table is covered by the elongate structure of the first and the second elongate element, and the fixed angular position between these elements. Furthermore, the secure fixations (the first elongate element to the second elongate element, the second elongate element to the base element, the base element to the operating table) provide for a robust structure of the medical fixation device, such that the different elements of the device maintain their position when forces are exerted thereon by the surgical retractors. The structure of the medical fixation devices is providing these advantages furthermore with a minimum of parts and adjustable connections. As a result, the medical fixation device can be positioned very easy and fast in a desired fixed position in the space around the operating table.

It is a further advantage of the current invention that a medical fixation device can replace the need for a medical assistant to hold retractors. Where in the past, the assistant needed to ensure the fixation of two or more surgical retractors at certain specific positions, depending on the requirements of the operation, and the assistant needed to ensure an accurate displacement and fixation, this can now, by means of embodiments of the present invention, be done by the surgeon who can connect the surgical retractor to the medical fixation device and can determine the exact position and the applied force by themselves. Thus there is less need for assisting personnel, which may allow surgery to proceed when operation room staff is short, and allow more efficient surgery, in terms of time as well as economic cost (including salary costs).

In some embodiments of the invention, the medical fixation device is characterized in that the medical fixation device further comprises a connection part for connecting an end of the first elongate element to an end of the second elongate element, wherein the first elongate element and the connection part are configured to allow rotatable connection of the first elongate element relative to the connection part;

wherein the first elongate element and the connection part are further configured to allow secure fixation of the first elongate element to the connection part in at least one fixed angular position of the first elongate element relative to the second elongate element;

wherein the medical fixation device further comprises a means for the secure fixation of the first elongate element to the connection part by connecting the means to the first elongate element and the connection part, and wherein the first elongate element can only rotate with respect to connection part when the means for secure fixation is not connected to the first elongate element.

In some embodiments of the invention, the medical fixation device is characterized in that the first elongate element comprises a cylindrical tube, which is configured to be releasably connected to two or more surgical instruments, such as retractor devices. It is an advantage of the cylindrical shape that it facilitates connection of the surgical instruments, and sliding of the surgical instruments over the cylindrical surface of the first elongate element into the optimal position. Furthermore, in view of the cylindrical shape, the surgical instruments can be connected to the first elongate element equally well from any direction in the space around the operating table.

In some embodiments of the invention, the medical fixation device is characterized in that the first elongate element comprises two or more connection members, each of which configured to be releasably connected to one or more surgical instruments such as retractor devices and to confine the surgical instruments to a specific area of the first elongate element. Preferably, the said connection members are circumferential cylindrical indentations in the first elongate element, preferably in the cylindrical tube of the first elongate element. It is an advantage of dedicated connection members that they enable confinement of the surgical instruments to a specific area of the cylindrical tube, minimizing the risk that the surgical instrument would displace during surgery. Additionally, connection members in form of circumferential cylindrical indentations facilitate connection of the surgical instruments to the medical fixation device from any point and/or direction in the space around the operating table, as well as rotation of the surgical instruments around the first elongate element. This enables fast and easy adjustment of the position of surgical instruments within the surgical site without the need to reconnect the surgical instrument to the medical fixation device and to lose additional time during surgery. These characteristics provide for a medical fixation device, which is even more intuitive and reliable in use.

In some embodiments of the invention, the medical fixation device further comprises an extension element configured for extending the first elongate element and configured to be releasably connected to the first elongate element. In some further embodiments, the extension element comprises a cylindrical tube. In some further embodiments the extension element comprises one or more connection members. In some further preferred embodiments, the one or more connection members are circumferential cylindrical indentations in the extension element, preferably in the cylindrical tube of the extension element. It is an advantage of the extension element that the length of the first elongate element and the number of connection members can be extended during surgery, such that the medical fixation device can be easily adapted and personalized to specific surgical circumstances and/or patient.

In some embodiments of the invention, the medical fixation device is characterized in that the second elongate element comprises a rectangular tube. In some further embodiments, the rectangular tube of the second elongate element is bended to form a first segment and a second segment wherein the first segment is at a fixed angle with respect to the second segment. It is an advantage of a rectangular tube that such tube is can withstand larger forces exerted thereon without bending over distance in comparison to for example a cylindrical tube. Therefore, a rectangular tube would be more rigid and resistant to displacement, and preserve better the original position when forces are exerted thereon by the first elongate element, connecting to the surgical instruments such as retractor devices. The bended aspect of the rectangular tube enables positioning of the medical fixation device in close proximity to the surgical site without restricting the access or the view at the surgical site for the surgeon. At the same time, the fixed angle makes the rectangular tube significantly more robust than if the angle was adjustable.

In some embodiments of the invention, the medical fixation device is characterized in that, the second elongate element is a high-type second elongate element or a low-type second elongate element, depending on the fixed angle of the first segment with respect to the second segment. It is an advantage of providing different types of the second elongate element, that the medical fixation device is more adaptable to an individual surgery or patient.

In some embodiments of the invention, the medical fixation device is characterized in that the base element comprises a cavity which is configured to receive a part of the second elongate element, and which is configured to receive the means for secure fixation of the part of the second elongate element in the cavity. It is an advantage that the cavity receives a part of the second elongate element, enclosing and securely fixing the second elongate element in the base element, which further minimizes displacement of the medical fixation device when forces are exerted thereon by the surgical instruments such as retractor devices.

In some further embodiments of the invention, the medical fixation device is characterized in that the cavity of the base element is configured such that the part of the second elongate element can slide into the cavity from at least two different sides of the base element. It is an advantage that the second elongate element can be inserted into both ends of the base element, since this enables symmetric positioning of the medical fixation device on either side of the operating bed, and towards either the head or the feet of the patient.

In some further embodiments of the invention, the medical fixation device is characterized in that the cavity of the base element is configured to allow receiving the second elongate element in two or more orientations of the second elongate element relative to the base element, in particular up-orientation, down-orientation or side-orientation, preferably up-orientation or down-orientation. It is an advantage that the second elongate element can be inserted into the base element in these orientations, since this provides flexibility as to the position and the orientation of the entire device, in particular the first elongate element connecting to the surgical instruments such as retractor devices, in the space around the operating table. Thus, by changing the orientation of the second elongate element and by choosing a different end of the base element cavity, different areas of the space around the operating table can be accessed by the medical fixation device.

In some further embodiments of the invention, the medical fixation device is characterized in that the cavity of the base element is a rectangular cavity, preferably a hollow rectangular tube, which is configured to receive a part of the rectangular tube of the second elongate element. It is an advantage that the shape of the receiving cavity matches the shape of the inserted tube, which further minimizes displacement of the medical fixation device when forces are exerted thereon by the surgical instruments.

In some embodiments of the invention, the medical fixation device is characterized in that the base element comprises a clamp which is configured for connecting the base element to the operating table and which is configured to receive the means for secure fixation of the clamp to the operating table. It is an advantage of using a clamp that it enables easy connection and secure fixation of the base element to the operating table, is compatible with different types of operating tables, and is a straight-forward, convenient and familiar design for the hospital personnel. A means for secure fixation of the clamp to the operating table in turn further stabilizes the medical fixation device when forces are exerted thereon by the surgical instruments.

In some embodiments of the invention, the medical fixation device is characterized in that the base element has a length of 80 mm to 250 mm, preferably 100 mm to 200 mm, more preferably 130 mm to 170 mm. It is an advantage of the chosen length that this provides sufficient support for robust and stable mounting of the medical fixation device on the operating table, while still being easy and convenient to move around, handle, connect and fix to the operating table.

In some embodiments of the invention, the medical fixation device is characterized in that the end of the first elongate element is directly connected to the end of the second elongate element. It is an advantage of such design that direct connection of the first elongate element to the second elongate element would enable simpler, more robust and more rigid connection, further minimizing displacement when forces are exerted on the medical fixation device by the surgical instruments.

In some embodiments of the invention, the medical fixation device is characterized in that the connection between the first elongate element and the connection part comprises a groove, preferably a groove with a shape corresponding to the shape of the outer surface of the first elongate element. It is an advantage of the described connection part that it makes the medical fixation device foldable, while at the same time preserving its robustness and resistance to displacement.

In some further embodiments of the invention, the medical fixation device is characterized in that the groove of the connection part has a length of 50 mm to 110 mm, preferably 60 mm to 100 mm, more preferably 70 mm to 90 mm. It is an advantage that the groove of the connection stabilizes the first elongate element for sufficient length, and is at the same time sufficiently compact for easy and light-weight packaging, transport and assembly.

In some further embodiments of the invention, the medical fixation device is characterized in that the connection between the first elongate element and the connection part comprises a pin joint configured to allow rotatable connection of the first elongate element to the connection part. It is an advantage of a pin joint that a pin joint is a one degree of freedom joint only allowing rotation motion, which thus minimizes any other unwanted motion in the other directions and further stabilizes the connection.

In some further embodiments of the invention, the medical fixation device is characterized in that the connection between the first elongate element and the connection part comprises a safety pin for secure fixation of the first elongate element in at least one fixed angular position relative to the second elongate element. It is an advantage that a safety pin enables secure fixation of the first elongate element relative to the second elongate element, but when necessary can also easily be removed, such the first elongate element can be rotated with respect to the second elongate element into the folded configuration of the medical fixation device.

In some further embodiments of the invention, the medical fixation device is foldable. It is an advantage of the folded configuration that the medical fixation device can be easily transported and stored in assembled state, and at the same time very easily and quickly set up in the operating room.

In some embodiments of the invention, the medical fixation device is characterized in that the first elongate element, the extension element, the second elongate element, the base element and/or the connection part are made of a metal, such as aluminum and/or stainless steel, and/or a resilient composite material, such as polyoxymethylene. It is an advantage of these materials that they are very resilient and robust, and at the same time able to withstand conventional sterilization conditions.

In some further embodiments of the invention, the medical fixation device is characterized in that the first elongate element, the second elongate element, the base element and the connection between the first elongate element and the second elongate element are configured such that, when fixed to the operating table and when forces of 90 N, in particular horizontal or vertical transversal forces, are exerted on the first elongate element, the displacement of the first elongate element relative to the operating table is less than 10 mm, preferably less than 7 mm, more preferably less than 5 mm. It is an advantage of a rigid medical fixation device that it will resist displacement when forces are exerted thereon, such that the final position of the surgical instrument is easy to assess and the movement of the device cannot distract the surgeon from the task at hand.

In another aspect, the present invention concerns a medical fixation device for connecting one or more surgical instruments such as retractor devices to an operating table in the space around the operating table, the medical fixation device comprising:

two elongate elements, a first elongate element and a second elongate element, a connection part for connecting the first elongate element to the second elongate element, a base element releasably connected to the second elongate element and configured to be connected to the operating table, a means for secure fixation of the second elongate element to the base element, and a means for secure fixation of the base element to the operating table, wherein the first elongate element is configured to be releasably connected to two or more surgical instruments, wherein the first elongate element and the connection part are configured to allow rotatable connection of the first elongate element relative to the connection part;

wherein the first elongate element and the connection part are further configured to allow secure fixation of the first elongate element to the connection part in at least one fixed angular position of the first elongate element relative to the second elongate element;

wherein the medical fixation device further comprises a means for the secure fixation of the first elongate element to the connection part by connecting the means to the first elongate element and the connection part, and wherein the first elongate element can only rotate with respect to connection part when the means for secure fixation is not connected to the first elongate element.

In a another aspect, the present invention concerns a medical device set comprising one or more medical fixation devices, preferably one or more medical fixation bars and one or more base elements, wherein a medical fixation bar is a medical fixation device without the base element. It is an advantage of the medical device set that the medical fixation devices which are necessary for one particular surgery can all be provided in one set, such that no additional time needs to be lost deciding how many devices would be necessary and collecting all necessary parts. This can not only reduce the installation and operation time, but also reduce the risk of mistakes.

In some further embodiments of the invention, the medical device set comprises one high-type medical fixation bar, one low-type medical fixation bar and two base elements. The inventors found that the combination of one high-type and one low-type medical fixation devices is typically sufficient to connect the necessary surgical instruments, in particular retractor devices, in particular for shoulder surgery. It is an advantage if these devices come as a pre-made set. Combining these two types of devices typically enables optimal positioning of the medical fixation devices and the connecting retractors, such that the surgeon has a good access and view to the surgical site, and at the same time can easily position and re-position the retractors in the space around the operating table.

In another aspect, the present invention concerns a medical device system for keeping open a wound during surgery comprising one or more medical fixation devices. Preferably, the medical device system further comprises one or more surgical instruments such as surgical retractors, one or more surgical drapes and/or one or more other medical devices for keeping open a wound during surgery. It is an advantage of a medical device system that different categories of devices which have to be used together for one purpose, in the case for keeping the wound open during surgery, are comprised in one system and optionally adjusted to one another. Medical device systems can help the hospital personnel know which devices to prepare for a surgery. This can reduce preparation time and minimize mistakes.

In a further aspect, the present invention concerns a method for installation of the medical fixation device or the medical device set.

In some embodiments of the invention, the present invention relates to a method for installation of the medical device set, the method comprising the steps of:

connecting the base element to the side of the operating table;

securely fixing the base element to the side of the operating table;

connecting the medical fixation bar to the base element;

securely fixing the medical fixation bar to the base element;

for each medical fixation device of the medical fixation device set.

In some embodiments of the invention, the method for installation of the medical device set, comprising one high-type medical fixation bar, one low-type medical fixation bar and two base elements, comprises the method for installation of installation of the medical device set, wherein the high-type medical fixation device is installed in the up-orientation on the contralateral side of the surgical site, and the low-type medical fixation device is installed in the down-orientation on the ipsilateral side of the surgical site. It is an advantage of the described installation method that it provides optimal accessibility to the surgical site, e.g. in shoulder surgery. Furthermore, the first elongate elements of the both fixation bars are also optimally positioned for connection to the surgical instruments such as retractor devices and easily accessible to the surgeon in the space around the operating table from the point where the surgeon normally stands to perform the surgery.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
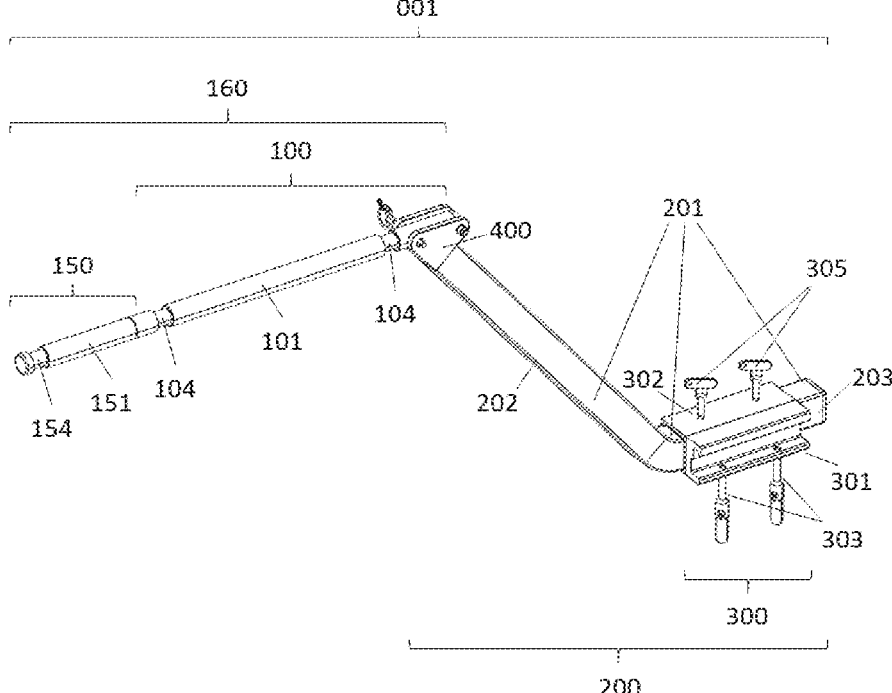
FIG. 1 illustrates a perspective view of the assembled medical fixation device 001.

The drawings are only schematic and are non-limiting. In the drawings, the size of some of the elements may be exaggerated and not drawn on scale for illustrative purposes. The dimensions and the relative dimensions do not correspond to actual reductions to practice of the invention.

Any reference signs in the claims shall not be construed as limiting the scope.

In the different drawings, the same reference signs refer to the same or analogous elements.

DETAILED DESCRIPTION OF THE INVENTION

The present invention will be described with respect to particular embodiments and with reference to certain drawings but the invention is not limited thereto but only by the claims.

The terms "up", "down", "high", "low", "horizontal", "vertical", "top", "bottom", "side" and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Definitions

As used herein, the term "medical device set" refers to a set comprising one or more medical fixation devices, preferably two or more medical fixation devices.

As used herein, the term "medical device system" refers to a system comprising one or more medical fixation devices in combination with other components. Other components may comprise, but are not limited to, one or more surgical instruments, one or more surgical drapes.

As used herein, the term "surgical instrument" refers to an instrument, which is used during surgery. In particular, the surgical instrument may comprise, but is not limited to, a retractor, a forceps, a pin, a clamp or any other medical device which enables the surgeon to hold biological tissue in a particular position and/or orientation in order to provide sufficient view and access to the surgical site for performing the procedure.

As used herein, the terms "retractor", "surgical retractor device", "surgical retractor" and "retractor device" are used interchangeably and refer to a surgical device for expanding the edges of the surgical incision for keeping the wound open in order to provide to the surgeon with sufficient view and access to the surgical site for performing the procedure. The said surgical retractor device may also comprise a self-retaining retracting system, such as a mechanical retracting system (e.g. as described in WO 2013/092938 A1), which may either form part of the surgical retractor device or be couplable to the surgical retractor device.

As used herein, the term "cylindrical tube" refers to a tube with a circular or an elliptical cross-section. It should be understood that the cylindrical tube can be hollow or solid. Therefore, the cylindrical tube includes also a cylindrical bar.

As used herein, the term "rectangular tube" refers to a tube with a square or a rectangular cross-section. A tube with a square cross-section is also referred to as a "square tube". The rectangular tube can be hollow or solid. Therefore, the rectangular tube includes also a rectangular bar.

As used herein, the term "medical fixation bar" refers to the assembled part of the medical fixation device without the base element.

As used herein, the term "screw" refers to any screw or bolt in the general meaning known to those skilled in the art. The screw may be threaded or not threaded. The screw may have a head or not have a head (e.g. set screw). The screw may comprise, but is not limited to, a screw, such as a wood screw, a machine screw, a thread cutting machine screw, a socket screw, a sheet metal screw, a set screw, a wing screw, a shelf screw; a bolt, such as a hex bolt, a carriage bolt, a lag bolt. The screw may further comprise a washer and/or a nut.

The terms "with respect to", and "relative to" are used interchangeably throughout the text.

The terms "opening", "through-opening", "hole" are used interchangeably throughout the text.

The terms "means for secure fixation", "secure fixation means", and "fixation means" are used interchangeably throughout the text.

As used herein, when a means for secure fixation of a first element in at least one fixed angular position relative to a second element is connected, this means that the means for secure fixation is in an "active position" keeping the first element at a fixed position relative to the second element. Accordingly, when a means for secure fixation of a first element in at least one fixed angular position relative to a second element is not connected, this means that the means for secure fixation is in an "inactive position" allowing rotational movement of the first element relative to the second element.

Medical Fixation Device

In a first aspect, the present invention relates to a medical fixation device for connecting one or more, preferably two or more, more preferably three or more, surgical instruments to an operating table in the space around the operating table for positioning biological tissue during surgery. In a first aspect, the present invention relates to a medical fixation device for connecting one or more surgical instruments such as retractor devices to an operating table in the space around the operating table for keeping open a wound during surgery.

By way of illustration and not limited thereto, embodiments of the medical fixation device 001 of the present invention, and standard and optional components of the medical fixation device, are depicted in FIGS. 1-10. The current invention further provides an alternative embodiment of the medical fixation device 1001, standard and optional components of which are depicted in FIGS. 13-24.

Figure 11:
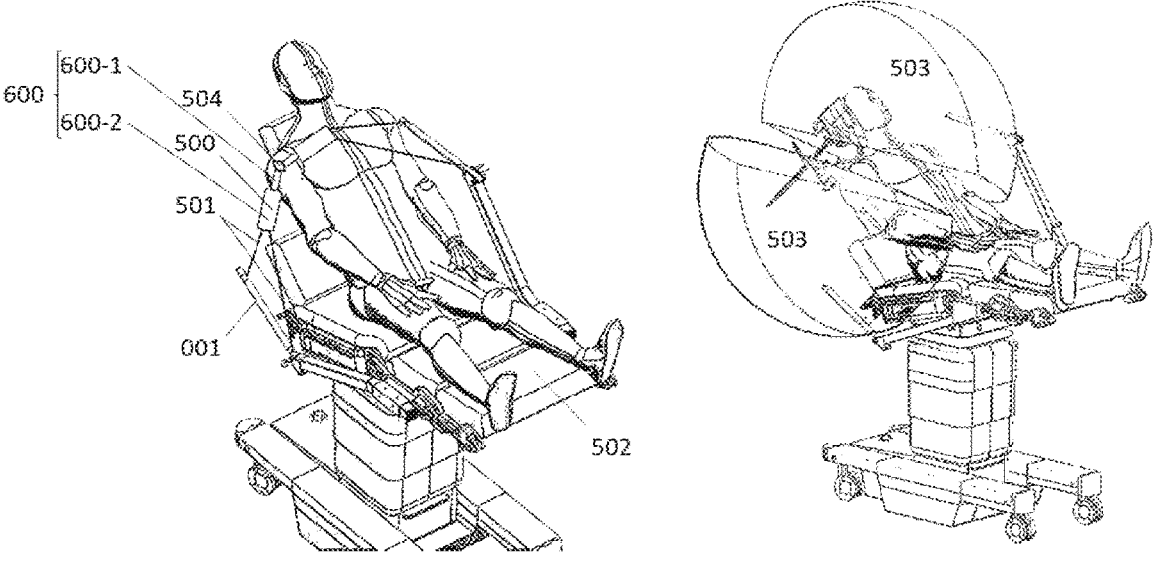
FIG. 11 illustrates on the left, a medical device system comprising a surgical instrument 600, in particular a retractor 500, connecting to the operating table 502 through medical fixation devices 001, and on the right, the coverage of the space 503 around the operating table by the medical fixation device.

FIG. 11 illustrates the medical fixation device 001, 1001 for connecting one or more surgical instruments 600, in particular one or more retractors 500, to an operating table 502 in the space 503 around the operating table. The medical fixation device 001, 1001 comprises two elongate elements, a first elongate element 100, 1100 and a second elongate element 200, 1200, and a base element 300, 1300 for connecting to the operating table 502.

The First Elongate Element

Figure 3:
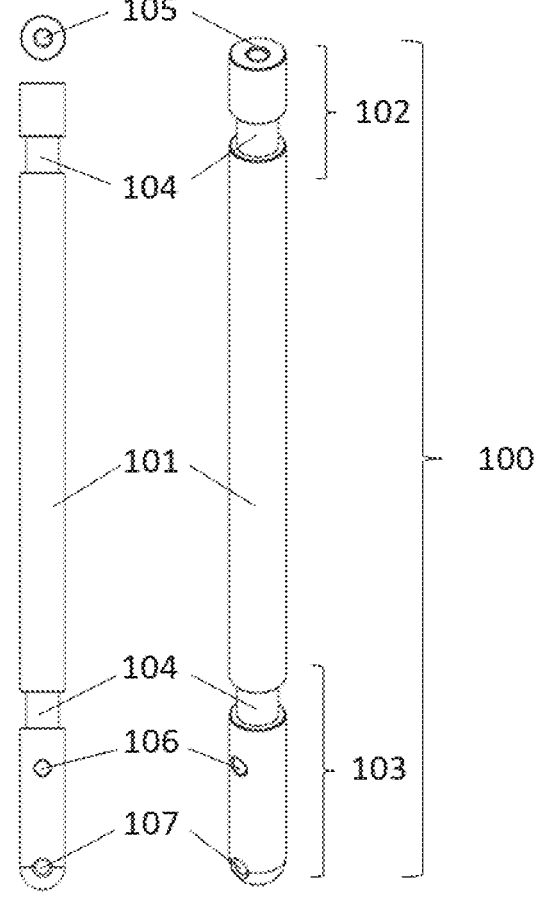
FIG. 3 illustrates the first elongate element 100.

By way of illustration and not limited thereto, embodiments of standard and optional components of the first elongate element 100 are depicted in FIG. 3. The first elongate element 100 typically comprises a tube 101, such as a cylindrical tube or a rectangular tube, preferably a cylindrical tube. Typically, the first elongate element would comprise a solid cylindrical tube. In an alternative embodiment, the tube may be hollow. For the purpose of the current invention, the first elongate element would typically have a length of 350 mm to 550 mm, preferably 400 mm to 500 mm, more preferably 430 mm to 470 mm. A rectangular tube would typically have a width of 15 mm to 35 mm, preferably 20 mm to 30 mm, more preferably 23 mm to 27 mm. A cylindrical tube would typically have a diameter of 15 mm to 35 mm, preferably 20 mm to 30 mm, more preferably 23 mm to 27 mm. These dimensions of the first elongate element allow for substantial coverage of the space around the operating table, while at the same time maintaining the robustness and resilience of the first elongate element when forces are exerted thereon by the surgical instruments, in particular retractor devices.

The first elongate element 100 is configured to be releasably connected to one or more surgical instruments 600, in particular one or more retractors 500. Preferably, first elongate element 100 is configured to be releasably connected to two or more, more preferably to three or more, surgical instruments 600 The surgical instrument typically comprises a connection piece 501 as illustrated in FIG. 11. The connection piece 501 can be of different types, such as a hook, a loop, a hole, a wire-like element, a combination of these, or any other connection piece, allowing connecting the surgical instrument 600 to the first elongate element 100.

In a particular embodiment, the first elongate element 100 comprises one or more, preferably two or more, more preferably three or more, connection members 104, each of which is configured to be releasably connected to one or more surgical instruments 600, in particular to the connection piece 501 of one or more surgical instruments 600. Preferably, the connection member 104 is configured to be releasably connected to one surgical instrument. In a particular embodiment, the connection member 104 is an indentation. For the purpose of the current invention, the indentation 104 would typically have a length of 10 mm to 30 mm, preferably 15 mm to 25 mm, more preferably 18 mm to 22 mm, and would typically have a depth of 2.0 mm to 5.0 mm, preferably 3.0 mm to 4.0 mm, more preferably 3.2 mm to 3.5 mm. The depth of the indentations 104 in chosen in such manner that it enables easy, stable and reliable connection of the surgical instrument 600, in particular the connection piece 501 of the surgical instrument, to the first elongate element 100, in particular the indentation 104. Preferably, the first elongate element 100 is covered by a surgical drape, such as for example MedEnvision EsySuit®. Preferably, the said connection piece 501 is a hook. In a preferred embodiment, the indentations 104 are circumferential indentations. In a preferred embodiment, the first elongate element 100 comprises a cylindrical tube 101, which comprises two or more, preferably three or more, circumferential indentations 104, in particular cylindrical circumferential indentations, as illustrated in FIG. 3.

Figure 4:
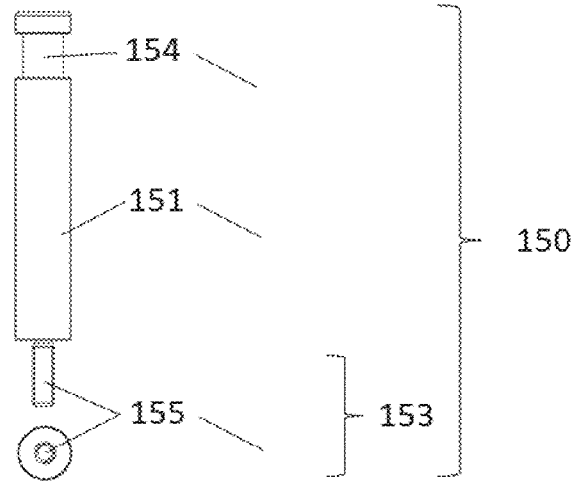
FIG. 4 illustrates the extension element 150.

To increase the length of the first elongate element 100 and/or to provide the first elongate element with additional connection members 104, an extension element 150 may be coupled onto the first elongate element 100 to form an extended first elongated element 160. By way of illustration and not limited thereto, embodiments of standard and optional components of the extension element 150, are depicted in FIG. 4. For the purpose of the current invention, the extension element 150 is considered an optional part. Therefore, all embodiments concerning the first elongate element 100 may optionally also comprise the extension element 150. In a particular embodiment, the medical fixation device 001 comprises an extension element 150, which is configured to be releasably connected to the first elongate element 100 and has a means for secure fixation of the extension element 150 to the first elongate element 100. In a particular embodiment, the first elongate element 100 comprises a female thread 105 at its first end 102 and the extension element 150 comprises a male thread 155 at the connecting end 153, which is configured to fit into the female thread 105 of the first elongate element 100. The extension element 150 typically comprises a tube 151, such as a cylindrical tube or a rectangular tube, preferably a cylindrical tube. Typically, extension element 150 may comprise a solid cylindrical tube. For the purpose of the current invention, the extension element 150 would typically have a length of 100 mm to 300 mm, preferably 150 mm to 250 mm, more preferably 160 mm to 200 mm. For the purpose of the current invention, the extension element 150 would typically have a similar shape, and a similar width or diameter, as the first elongate element 100. Additionally, the extension element 150 may comprise one or more connection members 154 with characteristics similar to the connection members 104 of the first elongate element 100. In a particular embodiment, the extension element 150 comprises one or more indentations 154, preferably circumferential indentations, preferably cylindrical circumferential indentations. In a further particular embodiment, the extension element 150 comprises an cylindrical tube 151 comprising one or more indentations 154, in particular cylindrical circumferential indentations.

The Second Elongate Element

Figure 5:
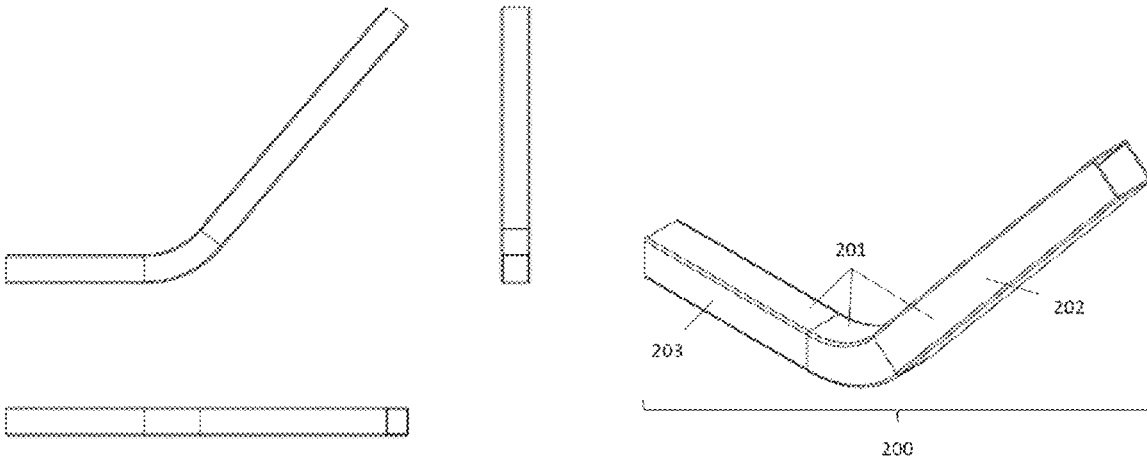
FIG. 5 illustrates the high-type second elongate element 200 in the up-orientation.
Figure 6:
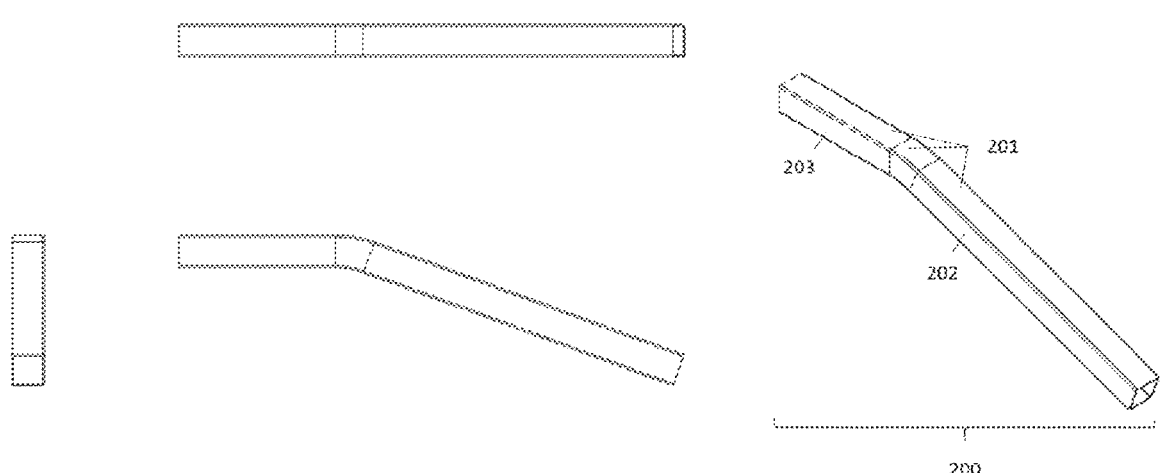
FIG. 6 illustrates the low-type second elongate element 200 in the down-orientation.

By way of illustration and not limited thereto, embodiments of standard and optional components of the second elongate element 200, are depicted in FIGS. 5 and 6. The second elongate element 200 typically comprises a tube 201, such as a cylindrical tube or a rectangular tube. In a preferred embodiment, the second elongate element 200 comprises a rectangular tube. In an alternative embodiment the second elongate element 200 comprises a cylindrical tube. Typically, the second elongate element would comprise a hollow rectangular tube. A hollow aspect of the second elongate element helps reducing the weight of the medical fixation device, facilitating its setup and manipulation during surgery. In an alternative embodiment the second elongate element 200 comprises a solid rectangular tube. For the purpose of the current invention, the second elongate element would typically have a length of 500 mm to 900 mm, preferably 600 mm to 800 mm, more preferably 650 mm to 750 mm. A rectangular tube would typically have a width of 20 mm to 60 mm, preferably 30 mm to 50 mm, more preferably 35 mm to 45 mm. A cylindrical tube would typically have a diameter of 20 mm to 60 mm, preferably 30 mm to 50 mm, more preferably 35 mm to 45 mm. These dimensions of the second elongate element allow for substantial coverage of the space around the operating table, while at the same time maintaining the robustness and resilience of the second elongate element when forces are exerted thereon by the first elongate element. In a particular embodiment, the second elongate element is a square tube. A square tube can withstand larger forces exerted thereon from different directions.

In a particular embodiment, the second elongate element 200 comprises a tube wherein the tube 201 is bended to form a first segment 202 and a second segment 203 wherein the first segment 202 is at a fixed angle with respect to the second segment 203. In a further particular embodiment, the tube is a rectangular tube, preferably a square tube. For the purpose of the current invention, the typical length of each segment would be 100 mm to 600 mm, preferably 150 mm to 500 mm, and the typical fixed angle between the two segments would be 100° to 175°, preferably 120° to 170°.

In a particular embodiment, the first segment 202 and the second segment 203 of the second elongate element 200 have a different length. In a further particular embodiment, the first segment is longer than the second segment. For the purpose of the current invention, the longer segment, preferably the first segment 202, would typically have a length of 300 mm to 600 mm, preferably 350 mm to 550 mm, more preferably 380 mm to 420 mm. The shorter segment, preferably the second segment 203, would typically have a length of 100 to 300 mm, preferably 150 mm to 250 mm, more preferably 170 mm to 210 mm.

In a particular embodiment, the second segment 203 of the second elongate element 200 is configured to be releasably connected to the base element 300.

To change the length and/or the fixed angle of the second elongate element 200, while preserving its rigid and resilient structure, it is possible to provide different types of the second elongate element. In a particular embodiment, the medical fixation device according to the invention may be a low-type or a high-type medical fixation device. A high-type second elongate element is characterized in that the first segment 202 is at a fixed angle of 100° to 145°, preferably 110° to 140°, more preferably 125° to 135° with respect to the second segment 203. A high-type medical fixation device or medical fixation bar comprises a high-type second elongate element. A low-type second elongate element is characterized in that the first segment 202 of the second elongate element is at a fixed angle of 146° to 175°, preferably 150° to 170°, more preferably 155° to 165° with respect to the second segment 203. Low-type medical fixation device or medical fixation bar comprise a low-type second elongate element. FIG. 5 illustrates a high-type second elongate element and FIG. 6 illustrates a low-type second elongate element.

The Base Element

Figure 7:
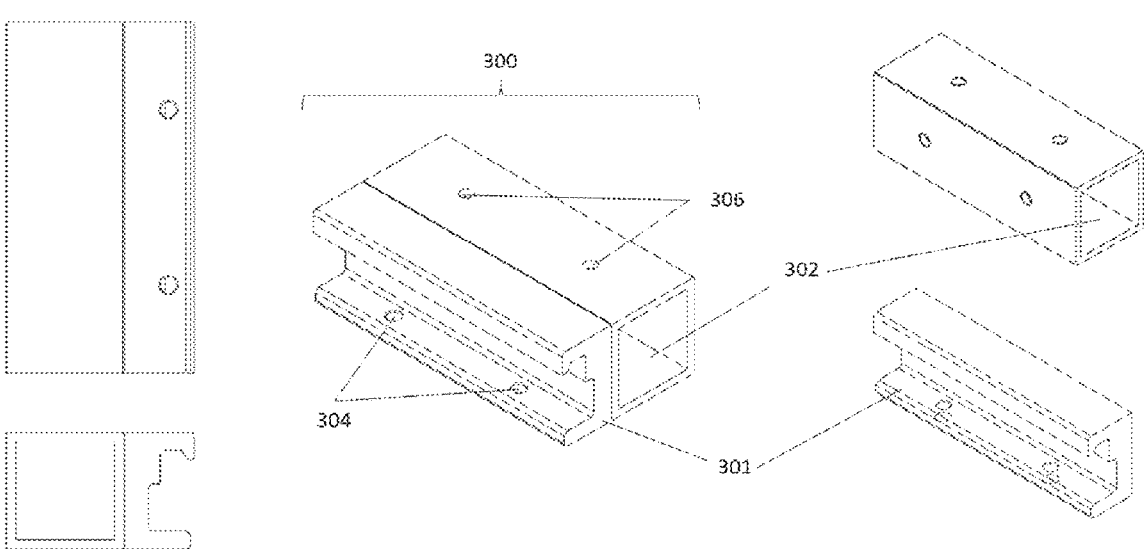
FIG. 7 illustrates the base element 300.

By way of illustration and not limited thereto, embodiments of standard and optional components of the base element 300, are depicted in FIG. 7. The base element 300 is configured to be connected to the operating table 502 and comprises a means 303 for secure fixation of the base element to the operating table. For the purpose of the current invention, the base element would typically have a length of 80 mm to 250 mm, preferably 100 mm to 200 mm, more preferably 130 mm to 170 mm. These dimensions allow for secure and stable fixation of the base element 300 to an operating table 502 and of the entire medical fixation device 001 onto the operating table 502 as well as secure and stable fixation of the second elongate element 200 to the base element 300.

In a particular embodiment, the base element comprises one or more clamps 301, preferably one clamp, which can be connected to the operating table 502 and which comprise a means for secure fixation 303 of the clamps to the operating table. In a particular embodiment, the one or more clamps 301 are configured to be releasably connected to the operating table, in particular to the rail of the operating table. For the purpose of the current invention, the one clamp would typically have a similar length as the base element. In a further particular embodiment, the one clamp 301 comprises two or more screws 303, preferably two screws, in two or more corresponding openings 304 for secure fixation of the clamp to the operating table, as illustrated in FIG. 1. The various types of screws suitable for secure fixation of the clamp to the operating table are known to those skilled in the art, and comprise but are not limited to, wing screws, shelf screws, bolts etc.

In a particular embodiment, the base element comprises a cavity 302 which is configured to receive the second elongate element 200, in particular a part of the second elongate element, and which comprises a means 305 for secure fixation of the second elongate element 200 to the base element. In a particular embodiment, the cavity 302 is configured to receive the tube 201 of the second elongate element 200. In a further particular embodiment, the base element 300 comprises a rectangular cavity 302, which is configured to receive the rectangular tube 201 of the second elongate element, and a means for secure fixation 305 of the second elongate element to the base element. In a preferred embodiment, the rectangular cavity 302 is configured to allow a translation movement of the second segment 202 of the second elongate element 200 relative to and into the rectangular cavity 302 of the base element 300 in the length direction of the second segment. Preferably, the cavity 302 of the base element (300) is configured, such that second elongate element 200 can slide into the cavity from at least two different sides of the base element. In some embodiments, the cavity 302 of the base element 300 is configured to allow receiving the second elongate element 200 in at least two orientations, wherein the orientations of the second elongate element 200 may comprise the first segment 202 pointing up, down or sideways with respect to the second segment 203 of the second elongate element when the second elongate element is received in the cavity 302. The different orientations, pointing up, down or sideways are referred to respectively as the up-orientation, the down-orientation and the side-orientation. Preferably, the second elongate element is slid into the cavity in the up-orientation or the down-orientation. The up-orientation and the down-orientation of the second elongate element are illustrated in FIG. 11 where the second elongate element on the left-hand side of the patient is in the up-orientation and the second elongate element on the right-hand side of the patient is in the down-orientation. Typically, the base element may comprise a hollow rectangular tube which is configured to receive a portion of the rectangular tube 201 of the second elongate element 200, and a means for secure fixation 305 of the second elongate element to the base element. FIG. 7 illustrates the hollow rectangular tube 302 and holes 306 for secure fixation of the second elongate element 200 to the base element 300 by screws, bolts, wing screws, shelf screws or any other fixation means known in the art. For the purpose of the current invention, the length of the hollow rectangular tube 302 may be the same as the length of the base element specified earlier in the current description. The internal width of the hollow rectangular tube 302 may correspond to the width of the rectangular tube 201 of the second elongate element 200 specified earlier in the current description, in particular to the width of the rectangular tube of the second segment 203 of the second elongate element.

In a particular embodiment, the cavity 302 which is configured to receive the second elongate element 200 may be provided in a part, in particular the hollow rectangular tube, which may be a separate element, which is releasably connected to the one or more clamps 301.

In a preferred embodiment, the base element 300 comprises one or more clamps 301 for connecting the base element to the operating table 502 and a cavity 302 for receiving the second elongate element 200. The one or more clamps 301, preferably one clamp, can be connected to the operating table 502 and comprise a means 303 for secure fixation of the clamps to the operating table. The cavity 302 is configured to receive the second elongate element 200, in particular the tube 201 of the second elongate element, and a means 305 for secure fixation of the second elongate element in the cavity of the base element.

The Connection Between the First and the Second Elongate Element

Referring to FIG. 1, the first elongate element 100 is rotatably connected to the second elongate element 200.

In a particular embodiment, the first elongate element 100 is directly connected to the second elongate element 200.

Figure 8:
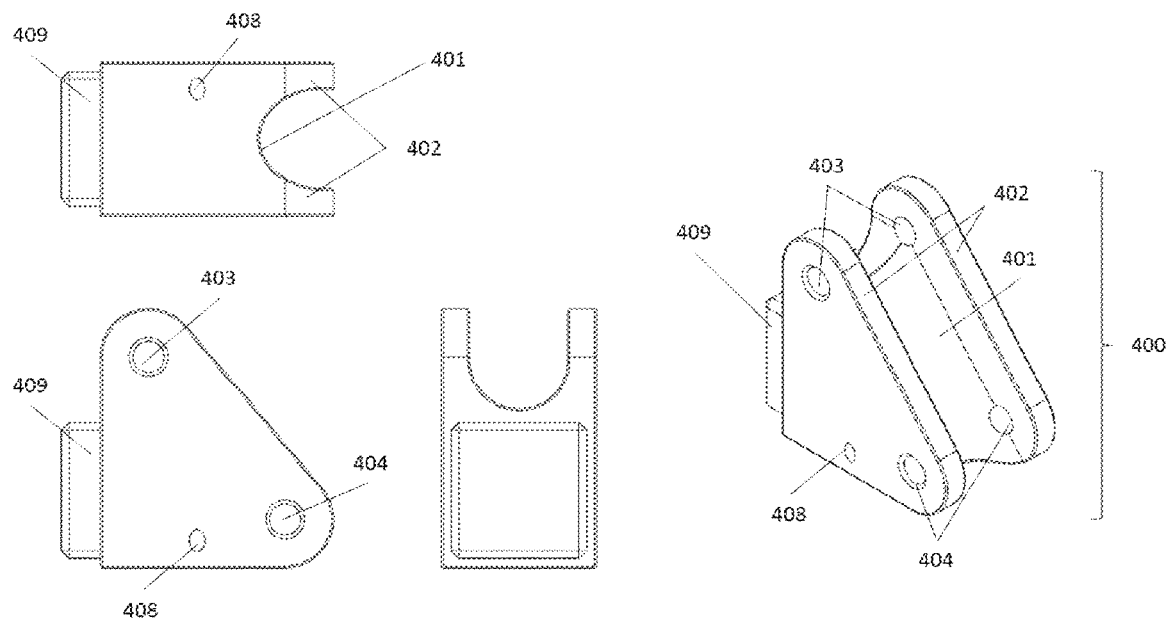
FIG. 8 illustrates the connection part 400 for connection between the first elongate element 100 and the second elongate element 200.

In another particular embodiment, the connection between the first elongate element 100 and the second elongate element 200 is made by a connection part 400. By way of illustration and not limited thereto, embodiments of standard and optional components of the connection part 400, are depicted in FIG. 8.

In a particular embodiment, the connection between the first elongate element 100 and the second elongate element 200, in particular the connection part 400, comprises a groove 401, which is configured to accommodate the first elongate element 100. The groove may have any shape corresponding to the shape of the outer surface of the first elongate element 100, in particular a shape corresponding to a cylindrical surface or a shape corresponding to a rectangular surface. For the purpose of the invention, the length of the groove would typically be 50 mm to 110 mm, preferably 60 mm to 100 mm, more preferably 70 mm to 90 mm. If the first elongate element 100 comprises a cylindrical tube 101, the groove 401 may have a rounded surface to correspond to the cylindrical surface of the cylindrical tube. If the first elongate element comprises a rectangular tube, the groove may have a U-shaped surface corresponding to part of the surface of the rectangular tube. For the purpose of the invention, the width or diameter of the groove would typically be corresponding to the width or diameter of the first elongate element. In a preferred embodiment, the connection part 400 between the first elongate element and the second elongate element comprises a groove with a rounded surface corresponding to part of the cylindrical surface of the cylindrical tube, hereafter referred to as cylinder-shaped groove, as illustrated in FIG. 8.

In a particular embodiment, illustrated for example on FIG. 1, the connection part 400 between the first elongate element 100 and the second elongate element 200 comprises a groove 401, preferably a cylinder-shaped groove, which is configured to accommodate the first elongate element 100, in particular the second end 103 of the first elongate element shown on FIG. 3. The connection part 400 may further comprise through-openings 403 corresponding to the means

Figure 2:
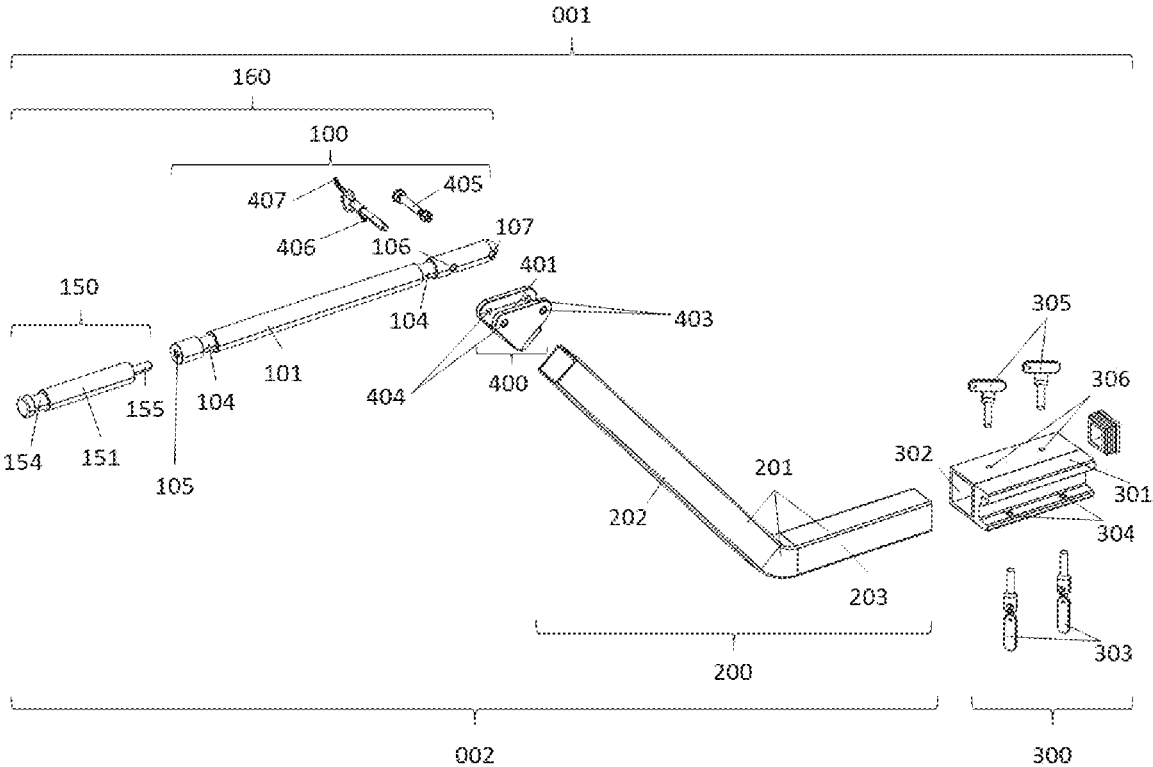
FIG. 2 illustrates an exploded view of the separate components of the medical fixation device 001, comprising the medical fixation bar 002 and the base element 300.

405 to rotatably connect the first elongate element 100 with the connection part 400 as illustrated for example on FIG. 2. And, the connection part 400 may comprise further through-openings 404 corresponding to the means 406 for secure fixation of the first elongate element 100 with the connection part 400 in at least one fixed angular position relative to the second elongate element 200. For the purpose of the invention, the distance between the through-opening 403 and the through-opening 404 on each side 402 of the groove 401 would typically be 30 mm to 80 mm, preferably 40 mm to 70 mm, more preferably 50 mm to 60 mm. Sufficient distance allows for strong fixation of the first elongate element 100 in at least one fixed angular position relative to the second elongate element 200. The means 405 to rotatably connect the first elongate element may be a pin joint inserted into the through-openings 403 of the connection part 400 and a through-opening 107 in the first elongate element. The through-opening 107 at the second end 103 of the first elongate element 100 is positioned in line with the set of two through-openings 403 on both sides 402 of the groove 401 and the pin 405 is configured to be inserted through the three through-openings 107, 403, 403 to rotatably fix the first elongate element 100 to the connection part 400 whereby the connection part is also connected to the second elongate element 200. In alternative embodiments, the rotatable connection may be realized by other means known in the art to create a rotatable connection. In a particular embodiment, the first elongate element comprises a second through-opening 106 at the second end 103 of the first elongate element for the secure fixation. The second through-opening 106 is positioned in line with the second set of two through-openings 404 positioned at both sides 402 of the groove. A safety pin 406 configured to be inserted through the three through-openings 106, 404, 404 releasably fixes the first elongate element 100 to the connection part 400 whereby the connection part is also connected to the second elongate element 200. The safety pin 406 may comprise a ball lock pin, a locking pin with a push button or any other pin which is configured to be inserted through the three through-openings and to releasably fix the first elongate element to the second elongate element through the connection part. In alternative embodiments, the secure fixation may be realized by other means known in the art to create a secure fixation. For the purpose of the invention, the distance between the means 405 for rotational connection of the first elongate element to the connection part 400, in particular a pin, and the means 406 for secure fixation of the first elongate element in at least one fixed angular position relative to the second elongate element, in particular a safety pin, would typically be 30 mm to 80 mm, preferably 40 mm to 70 mm, more preferably 50 mm to 60 mm.

Figure 10:
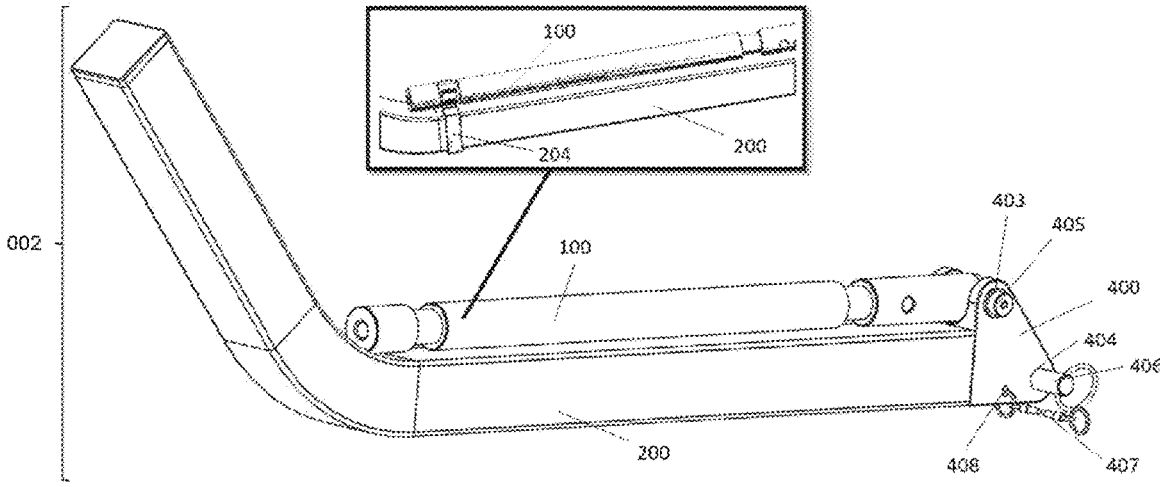
FIG. 10 illustrates the medical fixation bar 002 in folded configuration.

In a further particular embodiment, the safety pin 406 is connected to the medical fixation device 001, in particular to a safety through-opening 408 in the connection part 400, by means of a retention cable 407 as illustrated in FIG. 10. The retention cable 407 ensures that the safety pin does not fall on the ground or gets lost, when it is taken out of the through-openings. This is in particular important in a surgery environment.

For the purpose of the current invention, the connection part 400 would typically be configured such that the first elongate element 100 can rotatably connect at an angle of 0° to 160°, preferably 0° to 150°, more preferably 0° to 140° with respect to the second elongate element 200. The connection part 400 would typically be configured such that the first elongate element 100 can be securely fixed at an angle of 100° to 160°, preferably 110° to 150°, more preferably 120° to 140° with respect to the second elongate element 200.

Figure 9:
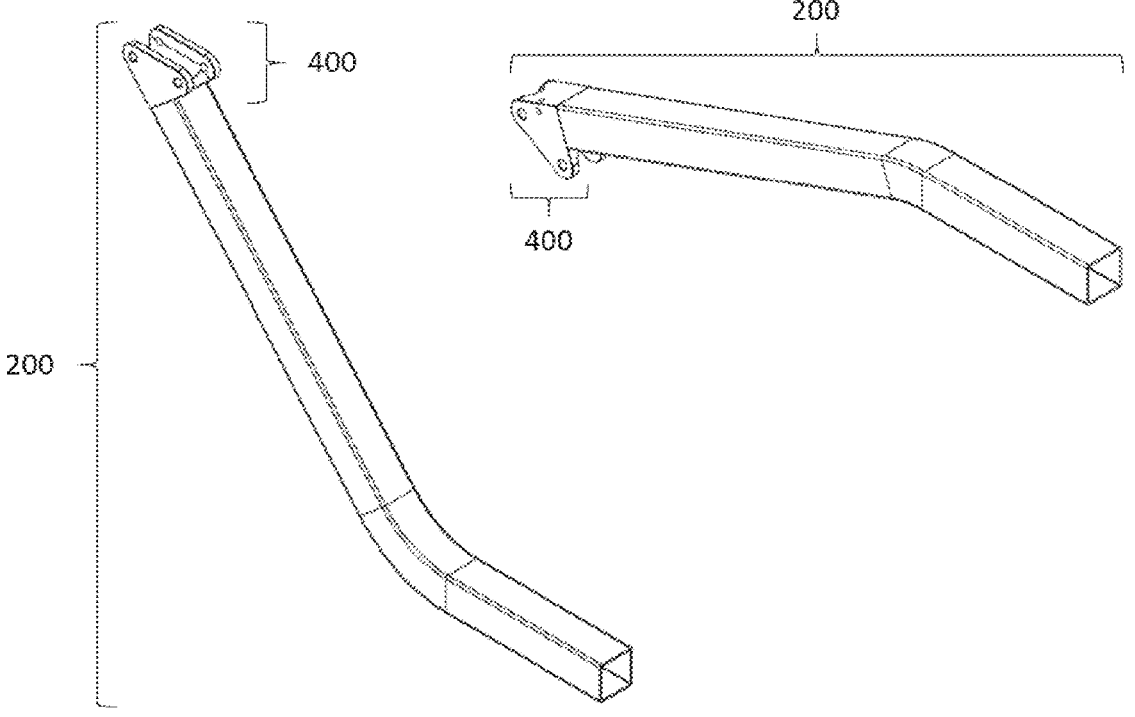
FIG. 9 illustrates the high-type second elongate element 200 (on the left) and the low-type second elongate element 200 (on the right), comprising the connection part 400.

In a particular embodiment, the described connection part 400, may be a separate element, which is releasably connected 409 to the second elongate element 200. In an alternative embodiment, the described connection part 400 may be part of the second elongate element 200, and in particular be located at the end of the second elongate element 200 as shown in FIG. 9.

Alternative Embodiment of the Medical Fixation Device

By way of illustration and not limited thereto, the standard and optional components of the alternative embodiment of the medical fixation device 1001 are depicted in FIGS. 13-23. As illustrated by the figures, in particular FIGS. 13a, 13b and 14, the medical fixation device 1001 is completely assembled. It is an advantage of the medical fixation device 1001, that it enables fast and easy setup of the device during surgery.

In the alternative embodiment, the medical fixation device 1001 comprises two elongate elements, a first elongate element 1100 and a second elongate element 1200, and a base element 1300 for connecting to the operating table, wherein the medical fixation device 1001 comprises a first hinge 1400, which is configured to enable rotatable connection and secure fixation of the first elongate element 1100 with respect to the second elongate element 1200, and wherein the second elongate element 1200 comprises a first segment 1202 and a second segment 1203, such that the first segment 1202 is at a fixed angle with respect to the second segment 1203 and such that this fixed angle can be changed between one or more fixed angular positions. Hereto, the medical fixation device 1001 in particular comprises two hinges: a first hinge 1400 between the first elongate element 1100 and the second elongate element 1200, and a second hinge 1700 within the second elongate element 1200.

The First Elongate Element

Figure 15:
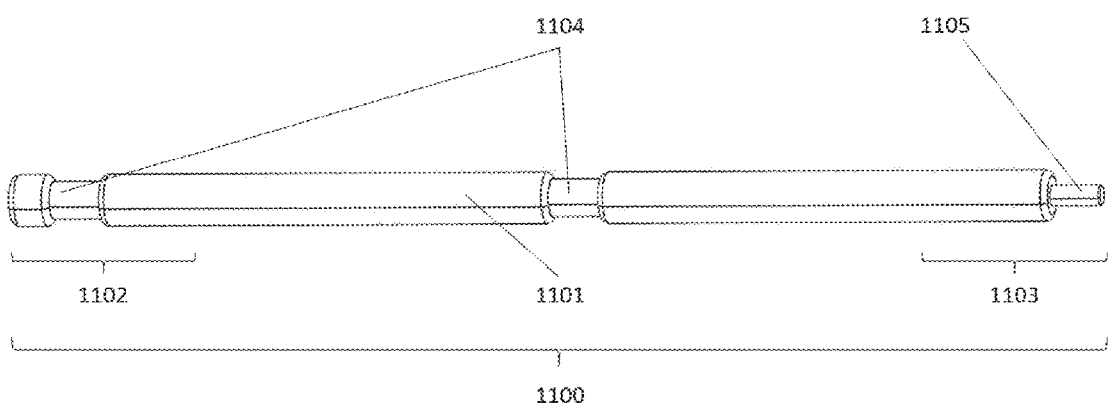
FIG. 15 illustrates the first elongate element 1100 according to the alternative embodiment.

By way of illustration and not limited thereto, embodiments of standard and optional components of the first elongate element 1100 are depicted in FIG. 15. The first elongate element 1100 typically comprises a tube 1101, such as a cylindrical tube or a rectangular tube, preferably a cylindrical tube. Typically, the first elongate element would comprise a solid cylindrical tube. In an alternative embodiment, the tube may be hollow. For the purpose of the current invention, the first elongate element would typically have a length of 450 mm to 850 mm, preferably 470 mm to 600 mm, more preferably 500 mm to 550 mm. A rectangular tube would typically have a width of 15 mm to 35 mm, preferably 20 mm to 30 mm, more preferably 23 mm to 27 mm. A cylindrical tube would typically have a diameter of 15 mm to 35 mm, preferably 20 mm to 30 mm, more preferably 23 mm to 27 mm. These dimensions of the first elongate element allow for substantial coverage of the space around the operating table, while at the same time maintaining the robustness and resilience of the first elongate element when forces are exerted thereon by the surgical instruments.

The first elongate element 1100 is configured to be releasably connected to one or more, preferably two or more, more preferably three or more surgical instruments 600. A surgical instrument can be chosen from the group of a retractor, a forceps, a pin, a clamp or any other surgical instrument which enables the surgeon to hold biological tissue in a particular position and/or orientation in order to provide sufficient view and access to the surgical site for performing the procedure. Preferably, the surgical instrument is a retractor 500. The surgical instrument would typically comprise two parts, wherein the first part 600-1 is configured to be in contact with biological tissue and the second part 600-2 is configured to be connectable to the medical fixation device. The biological tissue comprises, but is not limited to, skin tissue, fat tissue, muscle tissue, organ tissue, vessel tissue, nerve tissue, tendon tissue, cartilage tissue, or any other biological tissue, which can be relevant to move, position and/or orientate during surgery. The said surgical instrument 600, in particular the second part of the surgical instrument 600-2, may also comprise a self-retaining retracting system, such as a mechanical retracting system (e.g. as described in WO 2013/092938 A1), which may either form part of the surgical instrument or be couplable to the surgical instrument. The said surgical instrument 600, in particular the second part of the surgical instrument 600-2, more in particular the self-retaining retracting system, typically comprises a connection piece 601 as illustrated in FIG. 11. The connection piece 501 can be of different types, such as a hook, a loop, a hole, a wire-like element, a combination of these, or any other connection piece, allowing connecting the surgical instrument 600 to the first elongate element 1100.

In a particular embodiment, the first elongate element 1100 comprises one or more, preferably two or more, more preferably three or more, connection members 1104, each of which is configured to be releasably connected to one or more surgical instruments 600, such as surgical retractors 500, in particular to the connection piece 501 of one or more surgical instruments 600. Preferably, the first elongate element 1100 comprises two or more connection members 1104. More preferably, the first elongate element 1100 comprises three or more connection members 1104. In a particular embodiment, the connection members 1104 are indentations. For the purpose of the current invention, an indentation 1104 would typically have a length of 10 mm to 30 mm, preferably 20 mm to 30 mm, more preferably 23 mm to 27 mm, and would typically have a depth of 2.0 mm to 5.0 mm, preferably 3.0 mm to 4.0 mm, more preferably 3.2 mm to 3.5 mm. The depth of the indentations 1104 in chosen in such manner that it enables easy, stable and reliable connection of the surgical instrument 600, in particular the connection piece 501 of the surgical instrument, to the first elongate element 1100, in particular the indentation 1104. Preferably, the first elongate element 1100 is covered by a surgical drape, such as for example MedEnvision EsySuit®. Preferably, the said connection piece 501 is a hook. In a preferred embodiment, the indentations 1104 are circumferential indentations. In a preferred embodiment, the first elongate element 1100 comprises a cylindrical tube 1101, which comprises one or more circumferential indentations 1104, in particular one or more cylindrical circumferential indentations, as illustrated in FIG. 15.

The first elongate element (1100) is securely fixed in at least one fixed angular position relative the second elongate element (1200) by means of a means (1450) for secure fixation.

In a particular embodiment, the first elongate element 1100 is configured to be connected to the connection part 1400. The connection part 1400 is also referred to as the first hinge 1400. In particular, the first elongate element 1100 comprises a means 1105 for secure fixation of the connection part 1400 to the first elongate element 1100. In a particular embodiment, the first elongate element 1100 comprises a male thread 1105 at its second end 1103 and the connection part 1400 comprises a female threaded hole 1415, which is configured to accommodate the male thread 1105 of the first elongate element 1100. The male thread

Figure 16:
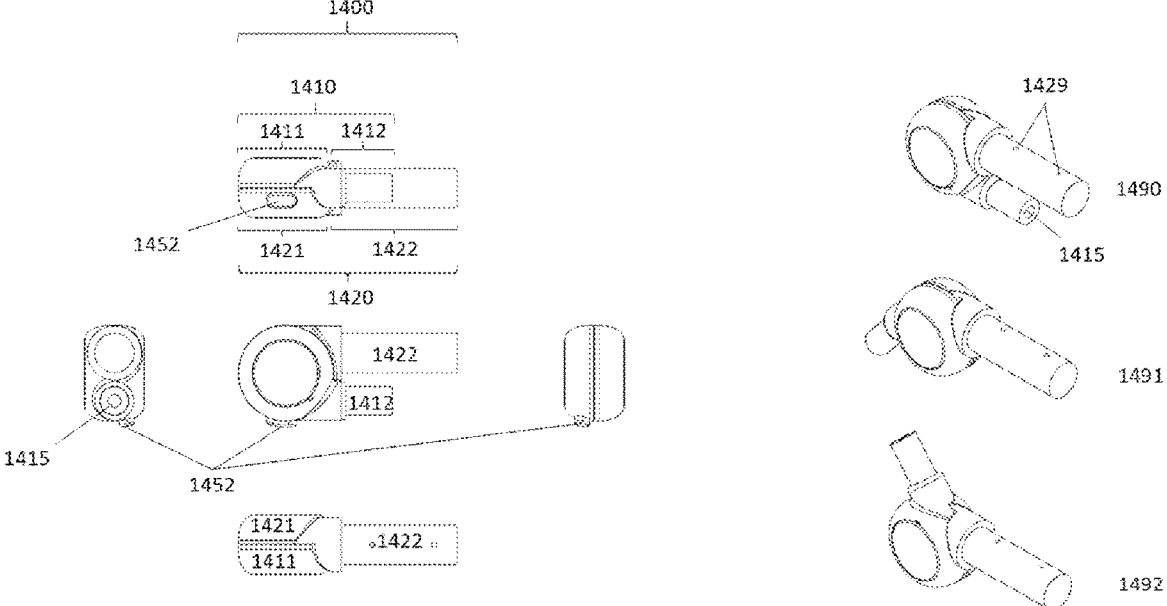
FIG. 16 illustrates different perspective views (on the left) and angular positions (on the right) of the first hinge 1400 for connection between the first elongate element 1100 and the second elongate element 1200 according to the alternative embodiment.

1105 is illustrated in FIG. 15. The female threaded hole 1415 is illustrated in FIG. 16. In a particular embodiment, shown in FIGS. 13-14, the connection between the first elongate element 1100 and the connection part 1400 forms one of the connection members 1104.

The First Hinge

Figure 13A:
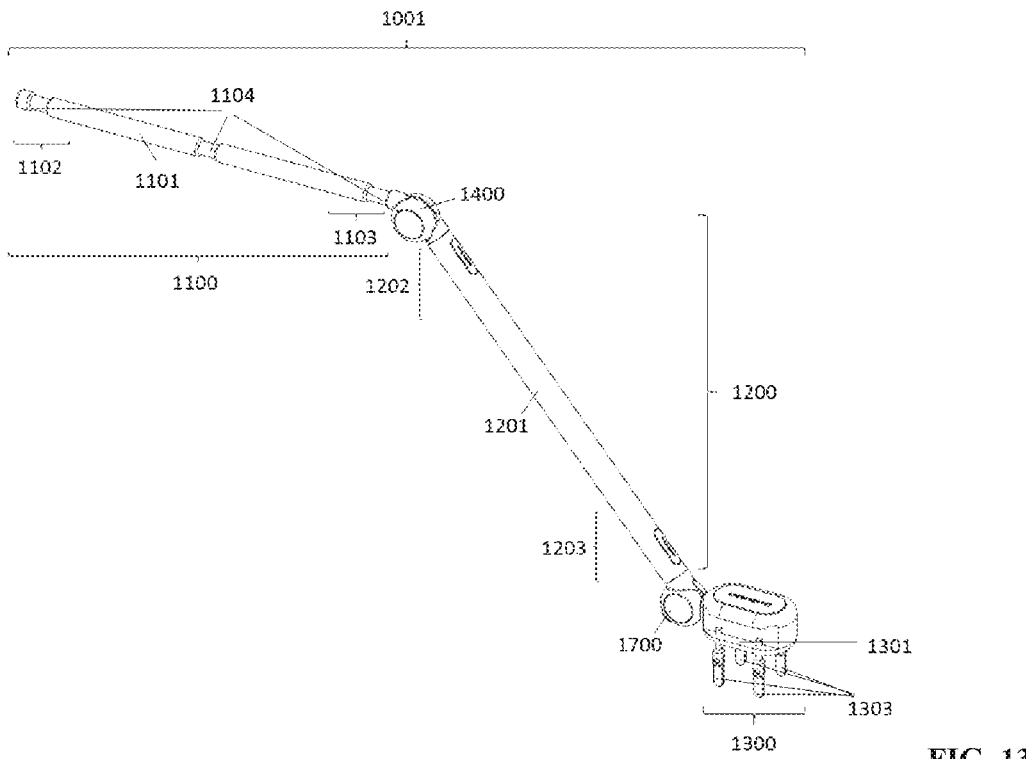
FIGS. 13a-13b illustrate a perspective view of the assembled medical fixation device 1001 according to the alternative embodiment.
Figure 13B:
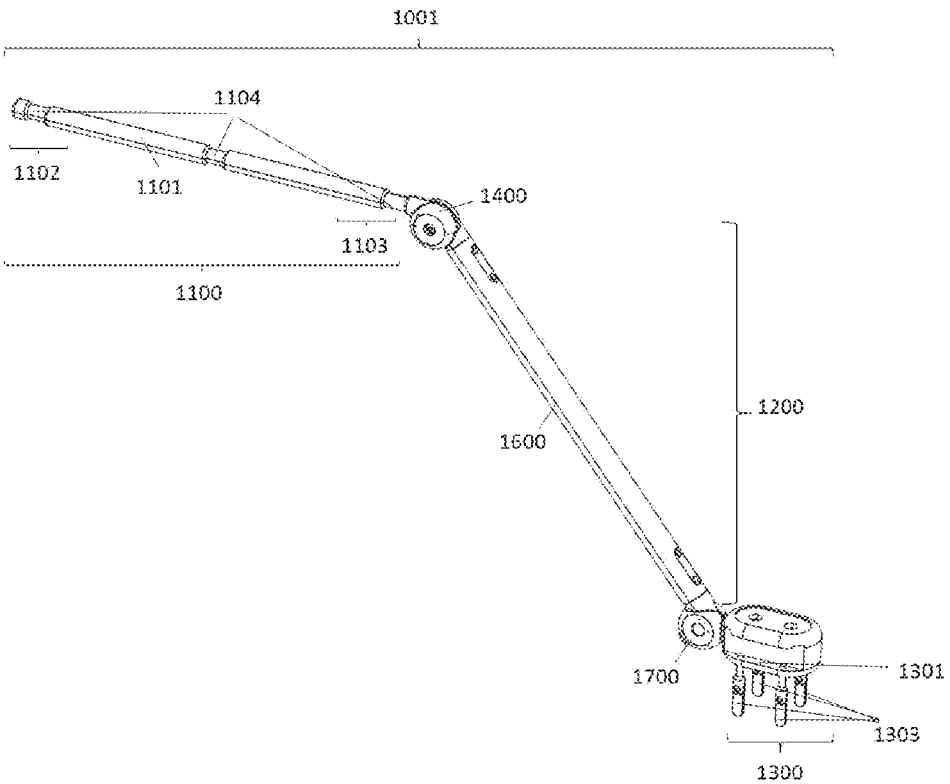
Figure 14:
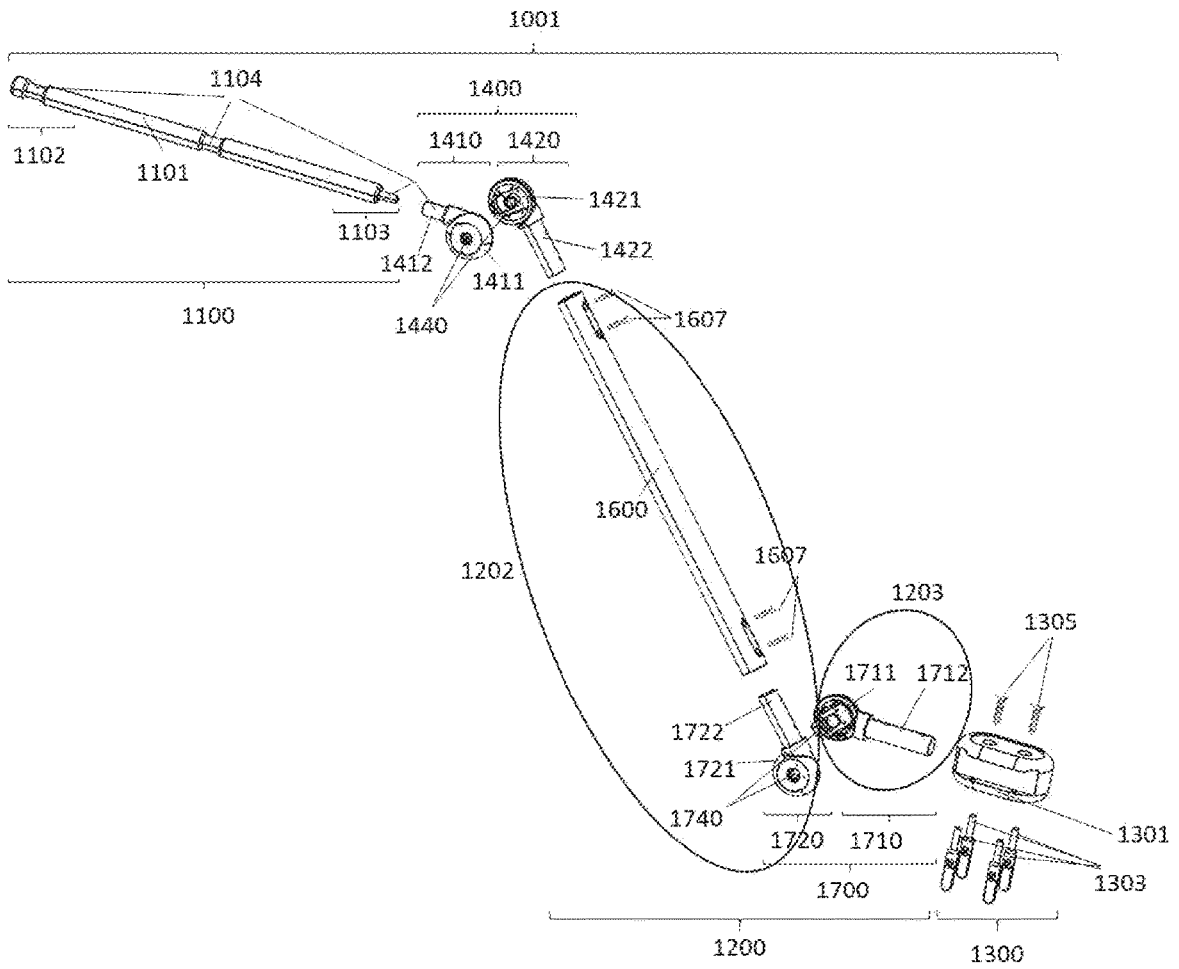
FIG. 14 illustrates an exploded view of the separate components of the medical fixation device 1001 according to the alternative embodiment.

Referring to FIGS. 13a, 13b and 14, the first elongate element 1100 is rotatably connected to the second elongate element 1200 by means of a connection part 1400. The connection part 1400 is also referred to as the first hinge 1400, such that the terms "connection part" and "first hinge" can be used interchangeably. By way of illustration and not limited thereto, embodiments of standard and optional components of the first hinge 1400, are depicted in FIGS. 16-18.

In a preferred embodiment, the first hinge 1400 is configured such that the first elongate element 1100 can rotatably connect relative to the second elongate element 1200 at an angle of 0° to 360°.

Figure 17:
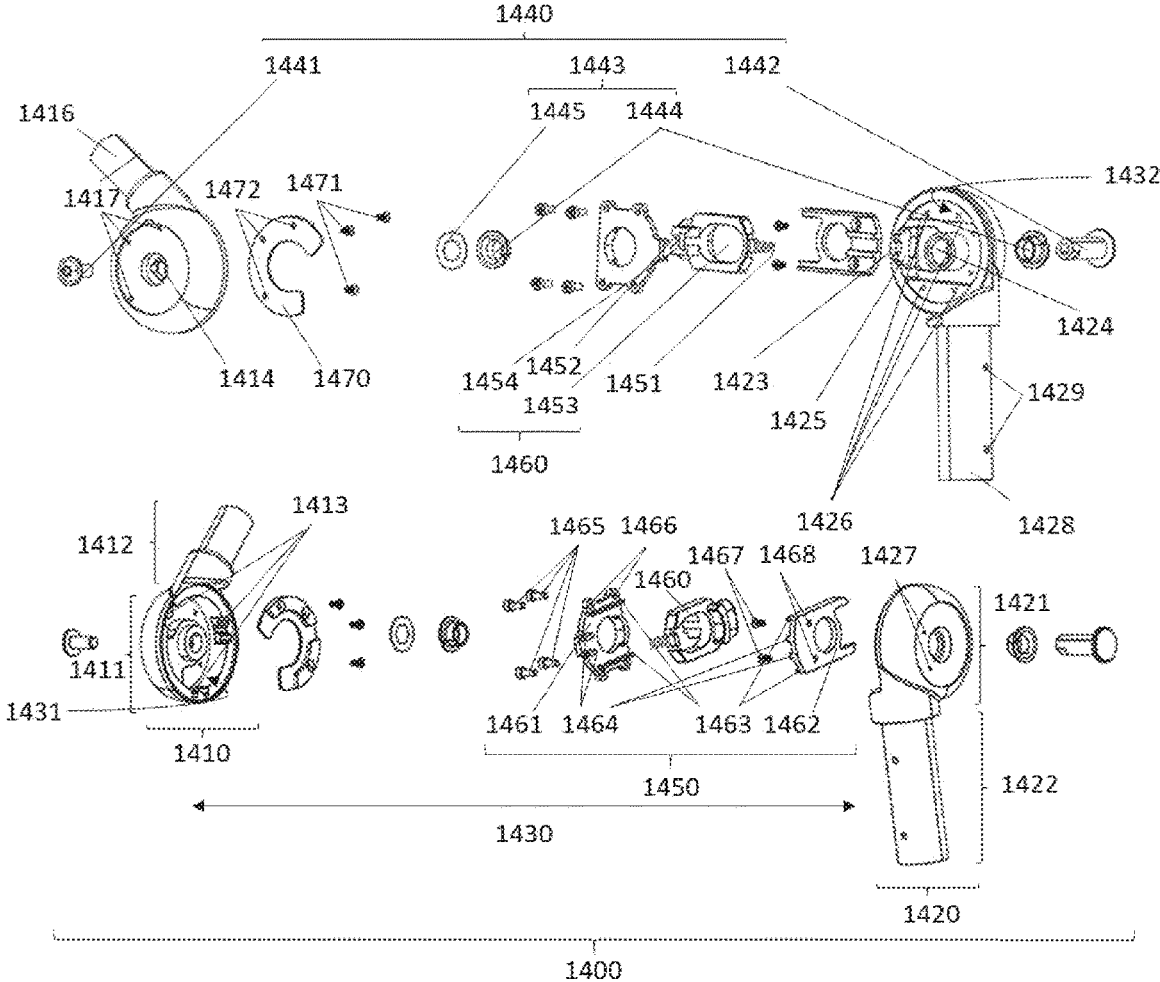
FIG. 17 illustrates an exploded view of the separate components of the first hinge 1400 according to the alternative embodiment.
Figure 18:
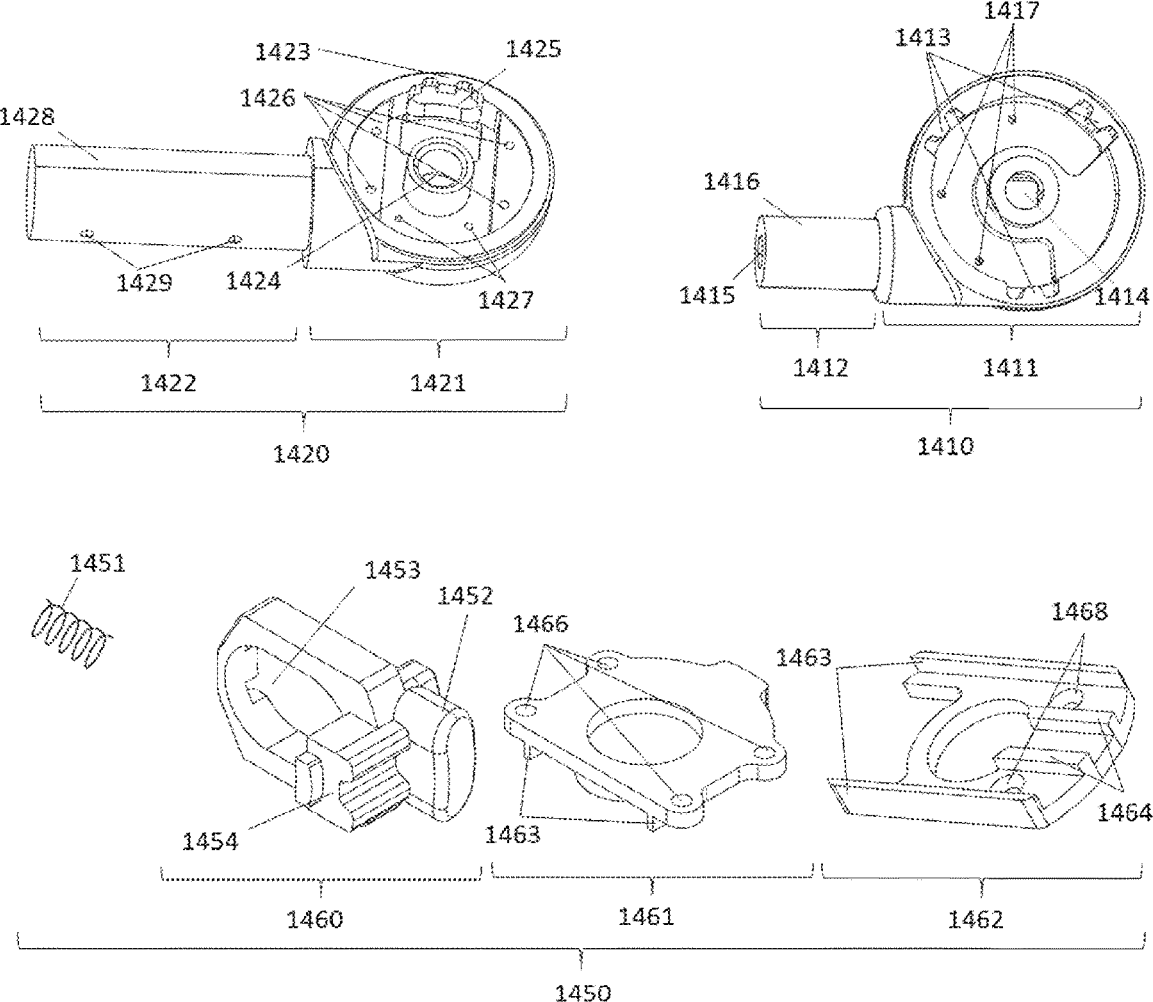
FIG. 18 illustrates in detail the separate components of the first hinge 1400 according to the alternative embodiment.

As shown in FIGS. 16-17, the first hinge 1400 comprises a base hinge part 1420 and a rotating hinge part 1410. In a particular embodiment, the base hinge part 1420 connects to the first elongate element 1100 and the rotating hinge part 1410 connects to the second elongate element 1200. In another particular embodiment, the base hinge part 1420 connects to the second elongate element 1200 and the rotating hinge part 1410 connects to the first elongate element 1100.

The rotating hinge part 1410 comprises a hinge segment 1411 and a connection segment 1412 Likewise, the base hinge part 1420 comprises a base hinge segment 1421 and a base connection segment 1422. The hinge segment 1411 and the base hinge segment 1421 form the parts which are rotatable with respect to each other within the first hinge 1400 and creating as such the rotatable connection. The connection segment 1412 and the base connection segment 1422 form the connection between on the one hand the first hinge 1400, and on the other hand the first elongate element 1100 and the second elongate element 1200.

The Hinge Segments

The hinge segment 1411 of the rotating hinge part 1410 and the base hinge segment 1421 of the base hinge part 1420 are configured to enable a rotatable connection of the rotating hinge part 1410 relative to the base hinge part 1420, and to enable secure fixation of the rotating hinge part 1410 to the base hinge part 1420 in at least one fixed angular position of the rotating hinge part 1410 with respect to the base hinge part 1420. The hinge segment 1411 and the base hinge segment 1421 may be hollow to form a hinge space 1430 between them when assembled. The hinge space 1430 is built up by a rotating hinge space 1431 in the rotating hinge part 1410 and a base hinge space 1432 in the base hinge part 1420. Preferably, the hinge segment 1411 and the base hinge segment 1421 have a hemispherical shape.

Rotatable Connection

In a particular embodiment, for example illustrated in FIG. 14, the first hinge 1400 comprises a pin joint, which is configured to enable rotatable connection of the rotating hinge part 1410 relative to the base hinge part 1420. In a further particular embodiment, for example illustrated in FIG. 17, the first hinge 1400 comprises an axis part 1440 which connects the rotating hinge part 1410 in particular the hinge segment 1411 to the base hinge part 1420 in particular the base hinge segment 1421. The axis part 1440 is for the most part located inside the hinge space 1430 and may be formed by a hollow protrusion.

In a further particular embodiment, the hinge segment 1411 of the rotating hinge part 1410 comprises an opening 1414 and the base hinge segment 1421 of the base hinge part 1420 comprises a corresponding base opening 1424, wherein the opening 1414 and the base opening 1424 are configured to receive the axis part 1440 which is configured to allow a rotating movement of the rotating hinge part 1410 relative to the base hinge part 1420 around the axis of the axis part 1440 when assembled. Together, the hinge segment 1411 with the opening 1414, the base hinge segment 1421 with the base opening 1424 and the axis part 1440 form the rotatable connection between the rotating hinge part 1410 and the base hinge part 1420.

In a further particular embodiment, the axis part 1440 comprises one or more screws. In a preferred embodiment, the axis part 1440 comprises a female screw 1442 and a male screw 1441 wherein the female screw 1442 is configured to accommodate the male screw 1441, such that when assembled together through the rotating hinge part 1410 and the base hinge part 1420, the rotating hinge part 1410 and the base hinge part 1420 can rotate relative to the axis part 1440. In a further particular embodiment, the axis part 1440 comprises axis guiding parts 1444. The axis guiding parts 1444 are configured to fit into the openings 1414 and 1424 of respectively the rotating hinge part 1410 and the base hinge part 1420. The axis guiding parts 1444 have themselves a central opening configured to receive the female screw 1442 which is assembled through these central openings with the male screw 1441. In a further particular embodiment, between the mail screw and the axis guiding part 1444, a washer 1445 is provided to allow easier rotation when assembled. The axis guiding parts 1444 and the washer 1445 form together an axis guiding system 1443 which stabilizes the axis part 1440 in the rotating hinge part 1410 and the base hinge part 1420 when assembled. Further, the axis guiding system 1443 sheaths the axis part 1440 from the other parts of the first hinge 1400.

In a preferred embodiment, the first hinge 1400 is configured, such that the rotating hinge part 1410 is rotatably connected to the base hinge part 1420 at an angle selectable from 0° up to 360°. In an embodiment of the invention, the selected angle somewhere between 0° and 360° is fixed by a means 1450 to keep the selected angle in the selected position.

Secure Fixation in at Least One Fixed Angular Position

In a particular embodiment, the first hinge 1400 comprises a means 1450 for secure fixation of the rotating hinge part 1410 under a certain angle relative to the base hinge part 1420. This means 1450 for secure fixation comprises in the embodiment of FIG. 17 a number of parts which may be assembled to the base hinge part 1420, to the rotating hinge part 1410, or to both. In a particular embodiment, the means 1450 for secure fixation comprises a hinge fixation means 1460, as shown in FIGS. 17-18.

In the embodiment of FIG. 17, the means 1450 for secure fixation is releasable by a fixation mechanism which is configured to allow rotation of the rotation hinge part 1410 relative to the base hinge part 1420 when the means 1450 for secure fixation is in an inactive position and to lock the rotation hinge part 1410 relative to the base hinge part when the means 1450 for secure fixation is in an active position. The means 1450 for secure fixation is configured to enable secure fixation of the rotating hinge part 1410 with respect to the base hinge part 1420 in at least one fixed angular position of the rotating hinge part 1410 with respect to the base hinge part 1420. Preferably, the means 1450 for secure fixation is located in the hinge space 1430. In a particular embodiment, to create the secure fixation of the rotating hinge part 1410 with respect to the base hinge part 1420 in at least one fixed angular position, the base hinge segment 1421 of the base hinge part 1420 comprises a base indentation 1423, and the hinge segment 1411 of the rotating hinge part 1410 comprises one or more rotating part indentations 1413, wherein the base indentation 1423 and the rotating part indentations 1413 are configured to receive a part of the hinge fixation means 1460 and wherein the simultaneous receiving of part of the hinge fixation means 1460 by the base indentation 1423 of the base hinge part 1420 and one of the rotating part indentations 1413 of the rotating hinge part 1410 results in the secure fixation of the rotating hinge part 1410 relative to the base hinge part 1420 in a fixed angular position. In a particular embodiment, the part of hinge fixation means 1460 which is receivable in the indentations is a dent 1454. Preferably, the hinge fixation means 1460 comprises the dent 1454. Preferably, the base indentation 1413 and the rotating part indentations 1423 are located inside the hinge space 1430. Preferably, the base and the rotating part indentations 1413, 1423 are U-shaped indentations, as illustrated in FIGS. 17-18, and the part of the hinge fixation means 1460 which is receivable in the indentations 1413, 1423, in particular the dent 1454, has a shape corresponding to the shape of the indentations. Accordingly, the embodiment where the indentations 1413, 1423 are U-shaped, the dent 1454 is also a U-shaped dent 1454, as illustrated in FIG. 18.

Within the context of the embodiment of FIG. 17, fixation in more than one fixed angular position is enabled by providing more than one rotating part indentations 1413 to create a medical fixation device 1001 wherein the rotating hinge part 1410 comprises more than one fixed angular position with respect to the base hinge part 1420. Preferably, the rotating hinge part 1410 comprises three or more rotating part indentations 1413.

In a particular embodiment, the rotating hinge part 1410 comprises three rotating part indentations 1413. In a preferred particular embodiment, as illustrated in FIG. 16, the three indentations 1413 enable secure fixation of the rotating hinge part 1410 in three fixed angular positions with respect to the base hinge part 1420: a high angular position 1491, a low angular position 1492 and a folded angular position 1490. The high angular position 1491 is a fixed angular position of 100° to 160°, preferably 110° to 150°, more preferably 120° to 140°. The low angular position 1492 is a fixed angular position of 200° to 260°, preferably 210° to 250°, more preferably 220° to 240°. The folded angular position 1490 is a fixed angular position of 0° to 5°, preferably 0° to 1°, more preferably 0°. In a further preferred embodiment, the high angular position 1491 and the low angular position 1492 are conjugate angular positions.

In another particular embodiment, the rotating hinge part 1410 comprises more than one rotating part indentations 1413 at equal distances from each other, such as every 30°, every 15°, every 10°, every 5° or every 1°. This enables a greater adaptability of the fixed angular position to a unique subject and surgery.

In a particular embodiment, the hinge fixation means 1460, is configured to perform an axial translation movement relative to the indentations 1413, 1423. This can be realized by any means to obtain one-dimensional translational movement known in the art. Preferably, the axial translation movement of the hinge fixation means 1460 relative to the indentations 1413, 1423 is a one-dimensional axial translation movement. Thus, the axial translational movement of the hinge fixation means 1460 away from the indentations 1413, 1423 enables rotational movement of the rotating hinge part 1410 with respect to the base hinge part

1420. Accordingly, the axial translational movement of the hinge fixation means 1460 towards and into the indentations 1413, 1423 results in the secure fixation of the rotating hinge part 1410 in an angular position with respect to the base hinge part 1420.

In a particular embodiment, the fixation mechanism, in particular the means 1450 for secure fixation, is configured to enable automatic secure fixation of the rotating hinge part 1410 in an angular position with respect to the base hinge part 1420, when the base indentation 1423 is aligned with one of the rotating part indentations 1413. In a particular embodiment, for example in FIGS. 17-18, the fixation mechanism, in particular the means 1450 for secure fixation, comprises a force element 1451 which creates a force on the hinge fixation means 1460 in the axial translation direction towards the indentations 1413, 1423 causing the automatic axial translation movement of the hinge fixation means 1460 into the indentations 1413, 1423. This results in automatic secure fixation of the rotating hinge part 1410 in an angular position with respect to the base hinge part 1420 by means of the hinge fixation means 1460, when the base indentation 1423 of the base hinge part 1420 is aligned with one of the rotating part indentations 1413 of the rotating hinge part 1410. Preferably, the force element 1451 is a mechanical force element, more preferably a spring.

Switching Between Rotatable Connection and Secure Fixation

In a particular embodiment, for example in FIGS. 17-18, the fixation mechanism, in particular the means 1450 for secure fixation comprises a button 1452, which is configured to enable switching between allowing rotatable connection of the first elongate element 1100 relative to the second elongate element 1200, and securely fixing the first elongate element 1100 in at least one fixed angular position relative to the second elongate element 1200. Preferably, the first hinge 1400 comprises a button 1452, which is configured to enable switching between allowing the rotation of the rotating hinge part 1410 relative to the base hinge part 1420, and the secure fixation of the rotating hinge part 1410 relative to the base hinge part 1420 in at least one fixed angular position. This button 1452 enables easy and intuitive manipulation by the surgeon to quickly switch between rotational movement and secure fixation of the connection between the first elongate element 1100 and the second elongate element 1200, in particular the first hinge 1400, and thus to optimally position the medical fixation device for surgery with minimal effort. In a further particular embodiment, the hinge segment 1411 of the rotating hinge part 1410 and/or the base hinge segment 1421 of the base hinge part 1420 comprises a button opening 1425, which is configured to accommodate the button 1452 and to allow a user to press the button. In a preferred embodiment, the button 1452 is part of the hinge fixation means 1460 and is configured such that moving the button 1452 inwards causes the hinge fixation means 1460 to move in the axial translation direction out of the indentations 1413, 1423.

In a further particular embodiment, the means 1450 for secure fixation, in particular the hinge fixation means 1460, comprises an opening 1453, which is configured to accommodate the axis part 1440 when making the translation movement. In this way, the axis part 1440 passes through the hinge fixation means 1460 and helps guiding the movement.

In a further particular embodiment, as illustrated in FIG. 17, the axial translation movement of the hinge fixation means 1460 is realized by providing a button cover 1461 on one side of the hinge fixation means 1460 and a button base 1462 on the other side of the hinge fixation means 1460. The button cover 1461, the button base 1462 and the hinge fixation means 1460 are configured such that when assembled, the hinge fixation means 1460 can only move in one axial translation direction between the button cover 1461 and the button base 1462. In a further particular embodiment, the button cover 1461 and/or the button base 1462 comprise one or more guiding rails 1463, which are configured to prevent sideways movement of the hinge fixation means 1460. In a further particular embodiment, the button cover 1461 and/or the button base 1462 comprise one or more spring guides 1464, which are configured to guide the force element 1451, in particular the spring, when compressed and de-compressed in the axial translation direction. The spring guides 1464 may also be configured to create the end position of the hinge fixation means 1460 when moved away from the indentations 1413, 1423.

In a particular embodiment, as illustrated in FIG. 17, the button base 1462 is assembled to the base hinge segment 1421 of the base hinge part 1420 through one or more openings 1468. The first hinge 1400 comprises one or more fixation means 1467 to assemble the button base 1462 through the one or more openings 1468 in the button base 1462 and one or more corresponding openings 1427 in the base hinge segment 1421. Subsequently, once the button base 1462 is assembled, the hinge fixation means 1460 and force element 1451, in particular the spring, can be positioned in the button base 1462, and the button cover 1461 can be assembled over the hinge fixation means 1460. The button cover 1461 is assembled with one or more fixation means 1465 to the base hinge segment 1421 through the one or more openings 1466 in the button cover 1461 and one or more corresponding openings 1426 in the base hinge segment 1421. Alternatively, the button base 1462 and the button cover 1461 may be assembled to the hinge segment 1411 of the rotating hinge part 1410. Preferably, the fixation means 1465 and 1467 is a screw.

In a particular embodiment, as illustrated in FIG. 17, the hinge segment 1411 of the rotating hinge part 1410 is configured to assemble a slider 1470, which is configured to smoothly guide the rotation movement of the rotating hinge part 1410 with respect to the button cover 1461. In a further particular embodiment, the slider 1470 comprises one or more openings 1472 to be assembled with fixation means 1471. The fixation means 1471 securely fixes the slider 1470 to the hinge segment 1411 of the rotating hinge part 1410 through one or more openings 1472 in the slider 1470, and one or more corresponding openings 1417 in the hinge segment 1411.

In a preferred embodiment, the means 1450 for secure fixation comprises the hinge fixation means 1460, the button cover 1461 and the button base 1462. In a further preferred embodiment, the hinge fixation means 1460 comprises the button 1452, the opening 1453 and the dent 1454. In further preferred embodiment, the base hinge segment 1421 of the base hinge part 1420 comprises the hinge fixation means 1460, the button cover 1461 and the button base 1462.

The Connection Segments

The connection segment 1412 of the rotating hinge part 1410 and the base connection segment 1422 of the base hinge part 1420 are configured to be connected to and securely fixed to either the first elongate element 1100 or the second elongate element 1200.

In a particular embodiment, the connection segment 1412 of the rotating hinge part 1410 is configured to be connected to and securely fixed to the second elongate element 1200, and the base connection segment 1422 of the base hinge part

1420 is configured to be connected to and securely fixed to the first elongate element 1100.

In another particular embodiment, the connection segment 1412 of the rotating hinge part 1410 is configured to be connected to and securely fixed to the first elongate element 1100, and the base connection segment 1422 of the base hinge part 1420 is configured to be connected to and securely fixed to the second elongate element 1200.

In a particular embodiment, the connection segment 1412 comprises a tube 1416 and the base connection segment 1422 comprises a tube 1428. Each of the tubes 1416, 1428 may be a cylindrical tube or a polygonal tube, preferably a cylindrical tube or a rectangular tube, more preferably a cylindrical tube. Preferably, each of the tubes 1416, 1428 is a solid tube. Alternatively, one or both of the tubes 1416, 1428 is a hollow tube.

In a further particular embodiment, for example in FIGS. 17-18, the connection segment 1412 or 1422, in particular the tube 1416 or 1428, which connects to the first elongate element 1100 comprises a means 1415 for secure fixation of the connection segment to the first elongate element 1100. Examples of means for secure fixation are well-known to a skilled person, and may comprise, but are not limited to, one or more screws, one or more bolts, glue, one or more clamps, one or more pipe couplings, or combinations of those. In a particular embodiment, the means 1415 for secure fixation of the first hinge 1400 to the first elongate element 1100 comprises a female threaded hole 1415, which is configured to accommodate the male thread 1105 of the first elongate element 1100. The female threaded hole 1415 is illustrated in FIGS. 16 and 18; the male thread 1105 is illustrated in FIG. 15.

In a further particular embodiment, the connection segment 1412 or 1422, in particular the tube 1416 or 1428, which connects to the second elongate element 1200 comprises one or more openings 1429, which are configured to accommodate the means 1207, in particular the screws, for secure fixation of the second elongate element 1200 to the first hinge 1400. Preferably the connection segment 1412 or 1422, comprises two or more openings 1429. More preferably, the connection segment 1412 or 1422, comprises two openings 1429, wherein the distance between the two openings 1429 is 20 mm to 60 mm, preferably 30 mm to 50 mm, more preferably 35 mm to 45 mm. Preferably, the connection segment 1412 of the rotating hinge part 1410 comprises the one or more openings 1429.

The Second Elongate Element

By way of illustration and not limited thereto, embodiments of standard and optional components of the second elongate element 1200, are depicted in FIGS. 19-22.

Figure 20:
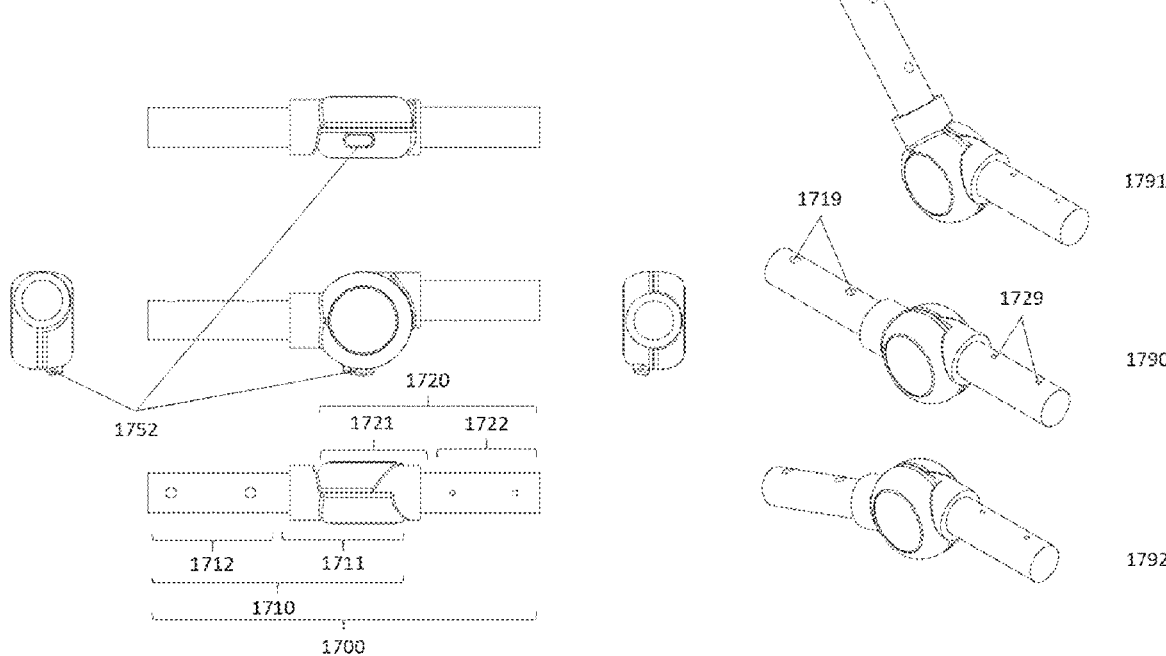
FIG. 20 illustrates different perspective views (on the left) and angular positions (on the right) of the second hinge 1700 of the second elongate element 1200 according to the alternative embodiment.
Figure 21:
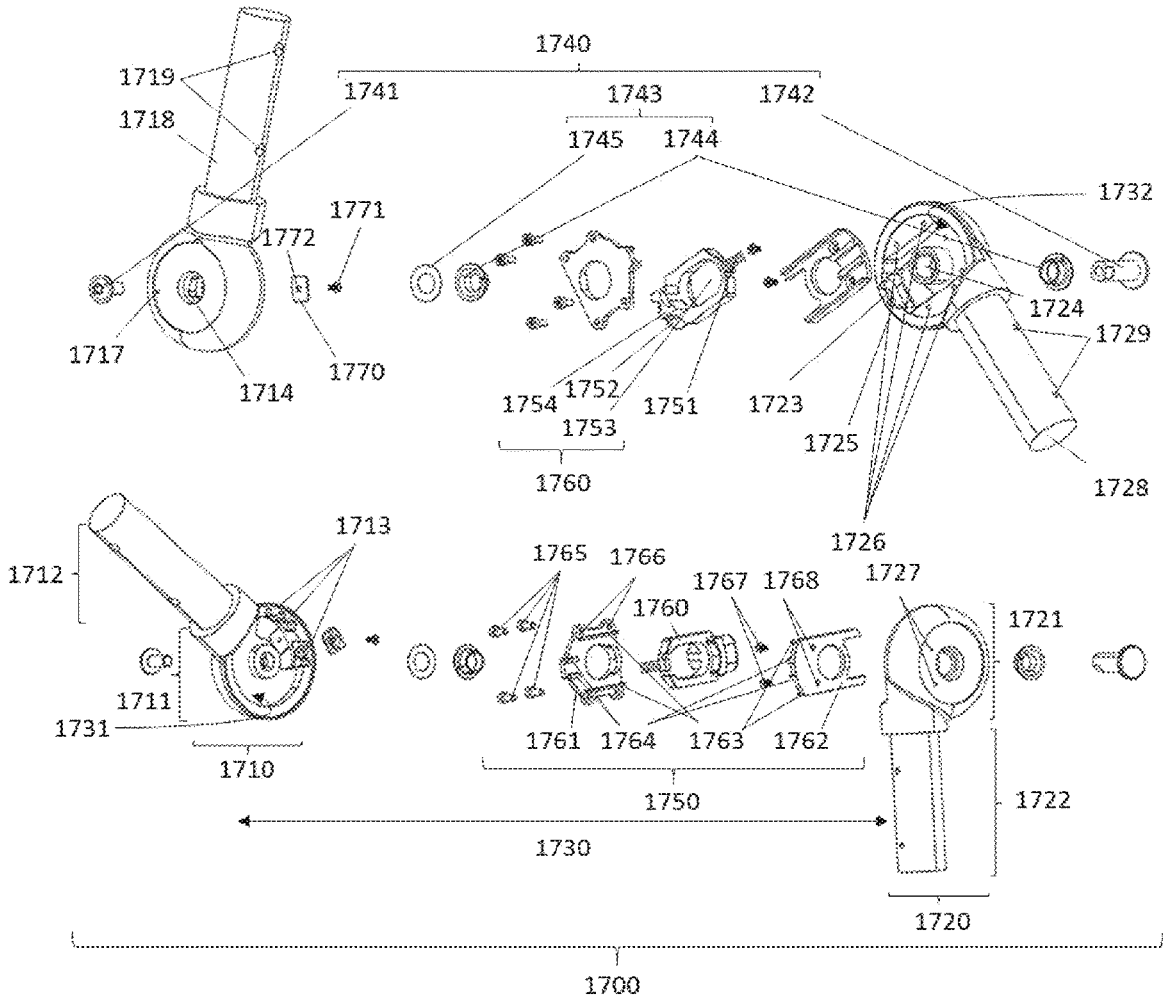
FIG. 21 illustrates an exploded view of the separate components of the second hinge 1700 according to the alternative embodiment.
Figure 22:
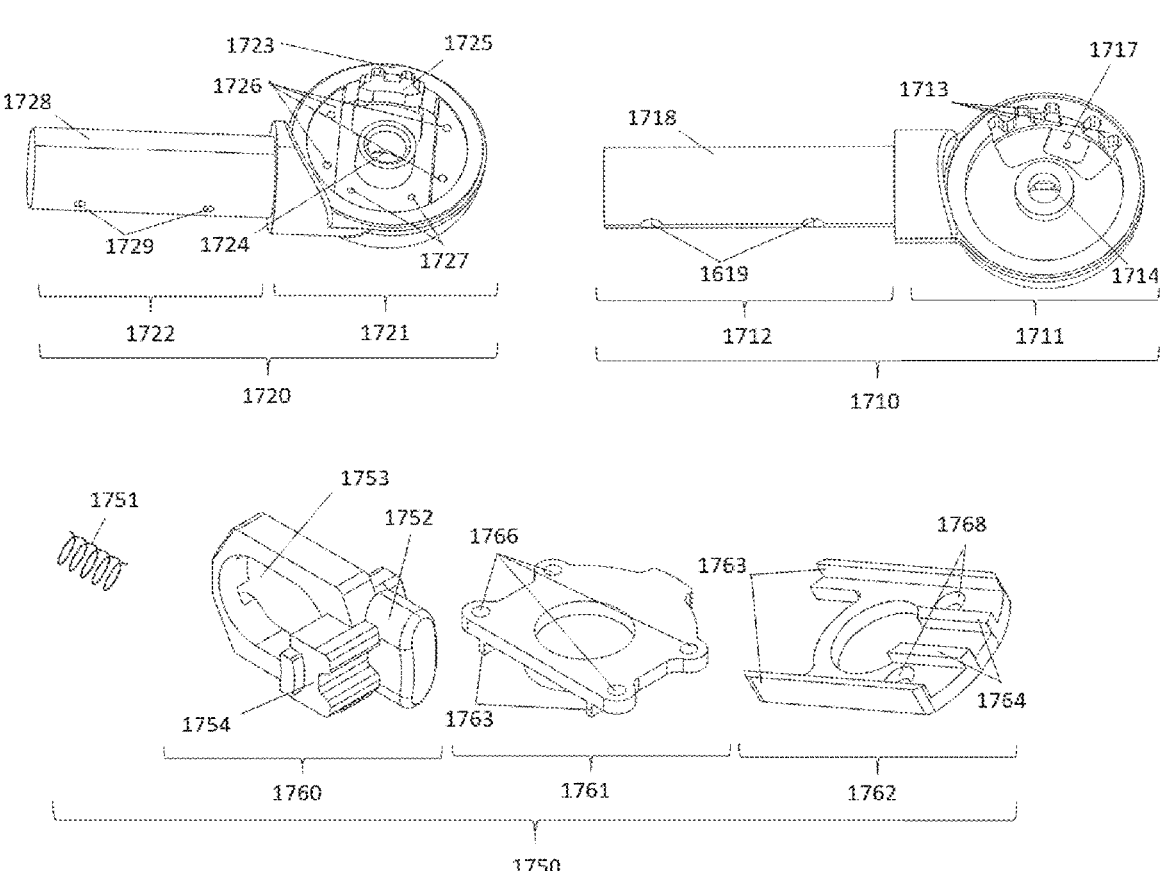
FIG. 22 illustrates in detail the separate components of the second hinge 1700 according to the alternative embodiment.

The second elongate element 1200 comprises a bar 1600 and a second hinge 1700. As shown in FIGS. 20-22, the second hinge 1700 comprises a base hinge part 1720 and a rotating hinge part 1710. The second hinge 1700 connects to the bar 1600 of the second elongate element 1200 and to the base element 1300, as shown in FIG. 14.

Figure 19:
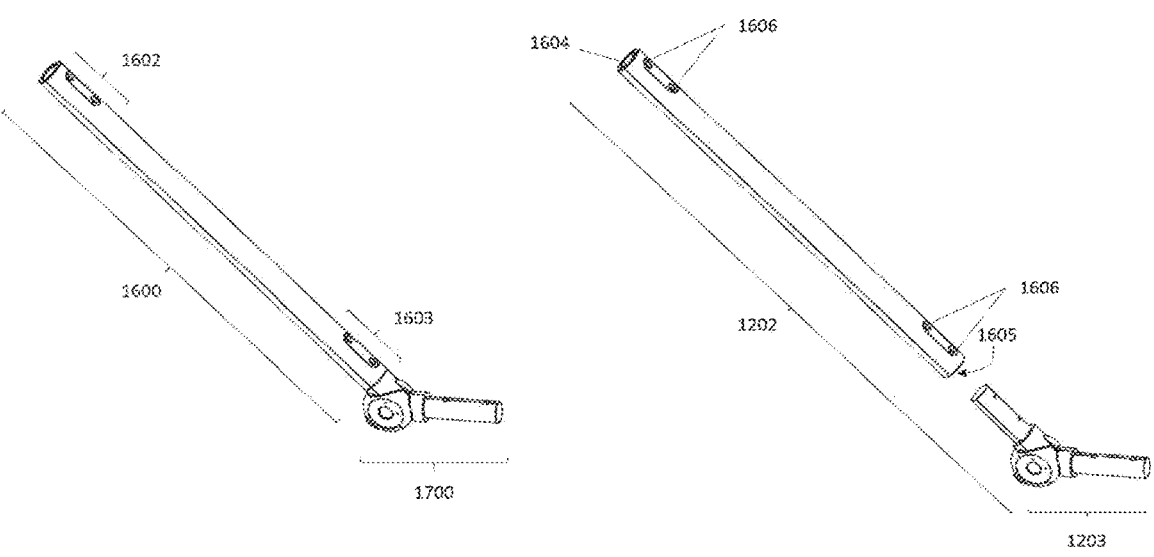
FIG. 19 illustrates the second elongate element 1200 according to the alternative embodiment.

As shown in FIG. 19, the second elongate element 1200 comprises a first segment 1202 and a second segment 1203, wherein the first segment 1202 can be fixed at a fixed angle with respect to the second segment 1203. The first segment 1202 is further configured to be connected to the first hinge 1400. The second segment 1203 is configured to be connected to the base element 1300. Preferably, the fixed angle of the first segment 1202 with respect to the second segment 1203 is adjustable between fixed angular positions. In a preferred embodiment, the second elongate element 1200 is configured to enable changing the fixed angle of the first segment 1202 with respect to the second segment 1203 between fixed angular positions. This can be realized by any means to position two segments at a fixed angle known in the art. In a particular embodiment, the second hinge 1700 is configured to enable changing the fixed angle causing that the first segment 1202 is at a fixed angle with respect to the second segment 1203 between fixed angular positions.

As shown in FIGS. 13*a*, 13*b* and 14, the bar 1600 and one of the hinge parts, the base hinge part 1720 or the rotating hinge part 1710, form a first segment 1202 of the second elongate element 1200 and the other hinge part, the rotating hinge part 1710 or the base hinge part 1720 respectively, forms a second segment 1203, wherein the first segment 1202 is at a fixed angle with respect to the second segment 1203. Preferably, the second elongate element 1200 is configured to enable changing the fixed angle of the first segment 1202 with respect to the second segment 1203 between two or more fixed angular positions. In particular, preferably, the second hinge 1700 is configured to enable changing the fixed angle of the first segment 1202 with respect to the second segment 1203 between two or more fixed angular positions.

In a particular embodiment, the base hinge part 1720 connects to the base element 1300 and the rotating hinge part 1710 connects to the bar 1600. In this embodiment, the rotating hinge part 1710 and the bar 1600 form the first segment 1202 of the second elongate element 1200 and the base hinge part 1720 forms the second segment 1203, wherein the first segment 1202 is at a fixed angle with respect to the second segment 1203.

In another particular alternative embodiment, the base hinge part 1720 connects to the bar 1600 and the rotating hinge part 1710 connects to the base element 1300. In this embodiment, the base hinge part 1720 and the bar 1600 form the first segment 1202 of the second elongate element 1200 and the rotating hinge part 1710 forms the second segment 1203, wherein the first segment 1202 is at a fixed angle with respect to the second segment 1203.

The Bar

The bar 1600 is typically a cylindrical bar or a rectangular bar, preferably a cylindrical bar. Typically, the second elongate element would comprise a hollow cylindrical bar. A hollow aspect of the second elongate element helps reducing the weight of the medical fixation device, facilitating its setup and manipulation during surgery. In an alternative embodiment the second elongate element 1200 comprises a solid cylindrical or rectangular bar. For the purpose of the current invention, the bar 1600 of the second elongate element 1200 would typically have a length of 300 mm to 600 mm, preferably 500 mm to 600 mm, more preferably 525 mm to 575 mm. A rectangular bar would typically have a width of 20 mm to 60 mm, preferably 30 mm to 50 mm, more preferably 30 mm to 40 mm. A cylindrical bar would typically have a diameter of 20 mm to 60 mm, preferably 30 mm to 50 mm, more preferably 30 mm to 40 mm. These dimensions of the bar 1600 of the second elongate element 1200 allow for substantial coverage of the space around the operating table, while at the same time maintaining the robustness and resilience of the second elongate element when forces are exerted thereon by the first elongate element. In a particular embodiment, the bar of the second elongate element 1200 is a circular bar.

The bar 1600 of the second elongate element 1200 is configured to be connected to the first hinge 1400 and to the second hinge 1700. Preferably, the bar 1600 comprises a first cavity 1604 at the first end 1602, which is configured to receive a part of the first hinge 1400, in particular the tube 1428 of the first hinge 1400, and a second cavity 1605 at the second end 1603, which is configured to receive a part of the second hinge 1700. In a preferred embodiment, the first cavity 1604 and the second cavity 1605 of the bar 1600 is a cylindric cavity. In an alternative embodiment, the first cavity 1604 and/or the second cavity 1605 of the bar 1600 is a polygonal cavity. Examples of polygonal cavities are well-known to those skilled in the art, and comprise, but are not limited to, a triangular cavity, a rectangular cavity, a pentagonal cavity, a hexagonal cavity, a heptagonal cavity, an octagonal cavity, a dodecagonal cavity. In a preferred alternative embodiment, the first cavity 1604 and/or the second cavity 1605 of the second elongate element 1200 is a rectangular cavity.

Furthermore, the second elongate element 1200 comprises a means 1607 for secure fixation of the first hinge 1400 and the second hinge 1700 to the bar 1600, as shown in FIG. 14. The means 1607 for secure fixation may comprise, but is not limited to, one or more screws, one or more bolts, glue, one or more clamps, or one or more pipe couplings. In a particular embodiment, shown in FIG. 19, the bar 1600 comprises one or more openings 1606 at the first end 1602 and at the second end 1603, wherein the openings 1606 are configured to accommodate the means 1607 for secure fixation. Preferably, the bar 1600 comprises two or more openings 1606 at each end 1602, 1603. Preferably, the openings 1606 and the means 1608 for secure fixation are identical on both ends 1602, 1603 of the bar 1600. Preferably, the openings 1606 at the first end 1602 of the second elongate element 1200 are aligned with the corresponding openings 1429 of the first hinge 1400, which are configured to accommodate the means 1607, in particular the screws, for secure fixation of the second elongate element 1200 to the first hinge 1400. In an alternative embodiment, the means 1607 for secure fixation may be part of the bar 1600.

In a particular embodiment, shown in FIG. 19, the bar 1600 comprises two openings 1606 at each end 1602, 1603 of the bar 1600. In a further particular embodiment, the openings 1606 are aligned in line with the axis of the bar 1600 and are identical on both ends 1602, 1603 of the bar 1600. In a further particular embodiment, the distance between the two openings 1606 at each end 1602, 1603 of the bar 1600 is 20 mm to 60 mm, preferably 30 mm to 50 mm, more preferably 35 mm to 45 mm. In a further particular embodiment, the two openings 1606 are at a distance of 10 mm to 30 mm, preferably 15 mm to 25 mm, more preferably 18 mm to 22 mm from each end 1602, 1603 of the bar 1600.

The Second Hinge

As shown in FIG. 19, the second elongate element 1200 comprises a bar 1600 and a second hinge 1700, which together form the first segment 1202 and a second segment 1203 of the second elongate element 1200, wherein the first segment 1202 is at a fixed angle with respect to the second segment 1203, and wherein the fixed angle is adjustable between two or more fixed angular positions.

By way of illustration and not limited thereto, embodiments of standard and optional components of the second hinge 1700, are depicted in FIGS. 20-22.

In a preferred embodiment, the second hinge 1700 is configured such that the first segment 1202 can rotatably connect relative to the second segment 1203 of the second elongate element 1200 at an angle of 0° to 360°.

As shown in FIGS. 20-22, the second hinge 1700 comprises a base hinge part 1720 and a rotating hinge part 1710. The second hinge 1700 connects to the bar 1600 of the second elongate element 1200 and to the base element 1300. In a preferred embodiment, the base hinge part 1720 connects to the base element 1300 and the rotating hinge part 1710 connects to the bar 1600. In an alternative embodiment, the base hinge part 1720 connects to the bar 1600 and the rotating hinge part 1710 connects to the base element 1300.

The rotating hinge part 1710 comprises a hinge segment 1711 and a connection segment 1712. Likewise, the base hinge part 1720 comprises a base hinge segment 1721 and a base connection segment 1722. The hinge segment 1711 and the base hinge segment 1721 form the parts which are rotatable with respect to each other within the second hinge 1700 and creating as such the rotatable connection. The connection segment 1712 and the base connection segment 1722 form the connection between on the one hand the second hinge 1700, and on the other hand the bar 1600 of the second elongate element 1200 and the base element 1300. Thus, rotatable connection within the second hinge 1700 enables positioning of the first segment 1202 of the second elongate element 1200 at a fixed, adjustable angle with respect to the second segment 1203, and the base element 1300, which is connected to the second segment 1203 of the second element 1200.

The Hinge Segments

The hinge segment 1711 of the rotating hinge part 1710 and the base hinge segment 1721 of the base hinge part 1720 are configured to enable a rotatable connection of the rotating hinge part 1710 relative to the base hinge part 1720, and to enable secure fixation of the rotating hinge part 1710 to the base hinge part 1720 in at least one fixed angular position of the rotating hinge part 1710 with respect to the base hinge part 1720. The hinge segment 1711 and the base hinge segment 1721 may be hollow to form a hinge space 1730 between them when assembled. The hinge space 1730 is built up by a rotating hinge space 1731 in the rotating hinge part 1710 and a base hinge space 1732 in the base hinge part 1720. Preferably, the hinge segment 1711 and the base hinge segment 1721 have a hemispherical shape.

Rotatable Connection

In a particular embodiment, for example illustrated in FIG. 14, the second hinge 1700 comprises a pin joint, which is configured to enable rotatable connection of the rotating hinge part 1710 relative to the base hinge part 1720. In a further particular embodiment, for example illustrated in FIG. 21, the second hinge 1700 comprises an axis part 1740 which connects the rotating hinge part 1710 in particular the hinge segment 1711 to the base hinge part 1720 in particular the base hinge segment 1721. The axis part 1740 is for the most part located inside the hinge space 1730 and may be formed by a hollow protrusion.

In a further particular embodiment, the hinge segment 1711 of the rotating hinge part 1710 comprises an opening 1714 and the base hinge segment 1721 of the base hinge part 1720 comprises a corresponding base opening 1724, wherein the opening 1714 and the base opening 1724 are configured to receive the axis part 1740 which is configured to allow a rotating movement of the rotating hinge part 1710 relative to the base hinge part 1720 around the axis of the axis part 1740 when assembled. Together, the hinge segment 1711 with the opening 1714, the base hinge segment 1721 with the base opening 1724 and the axis part 1740 form the rotatable connection between the rotating hinge part 1710 and the base hinge part 1720.

In a further particular embodiment, the axis part 1740 comprises one or more screws. In a preferred embodiment, the axis part 1740 comprises a female screw 1742 and a male screw 1741 wherein the female screw 1742 is configured to accommodate the male screw 1741, such that when assembled together through the rotating hinge part 1710 and the base hinge part 1720, the rotating hinge part 1710 and the base hinge part 1720 can rotate relative to the axis part 1740. In a further particular embodiment, the axis part 1740 comprises axis guiding parts 1744. The axis guiding parts 1744 are configured to fit into the openings 1714 and 1724 of respectively the rotating hinge part 1710 and the base hinge part 1720. The axis guiding parts 1744 have themselves a central opening configured to receive the female screw 1742 which is assembled through these central openings with the male screw 1741. In a further particular embodiment, between the mail screw and the axis guiding part 1744, a washer 1745 is provided to allow easier rotation when assembled. The axis guiding parts 1744 and the washer 1745 form together an axis guiding system 1743 which stabilizes the axis part 1740 in the rotating hinge part 1710 and the base hinge part 1720 when assembled. Further, the axis guiding system 1743 sheaths the axis part 1740 from the other parts of the second hinge 1700.

In a preferred embodiment, the second hinge 1700 is configured, such that the rotating hinge part 1710 is rotatably connected to the base hinge part 1720 at an angle selectable from 0° up to 360°. In an embodiment of the invention, the selected angle somewhere between 0° and 360° is fixed by a means 1750 to keep the selected angle in the selected position.

Secure Fixation in at Least One Fixed Angular Position

In a particular embodiment, the second hinge 1700 comprises a means 1750 for secure fixation of the rotating hinge part 1710 under a certain angle, in particular in a fixed angular position, relative to the base hinge part 1720. This means 1750 for secure fixation comprises in the embodiment of FIG. 21 a number of parts which may be assembled to the base hinge part 1720, to the rotating hinge part 1710, or to both. In a particular embodiment, the means 1750 for secure fixation comprises a hinge fixation means 1760, as shown in FIGS. 21-22.

In the embodiment of FIG. 21, the means 1750 for secure fixation is releasable by a fixation mechanism which is configured to allow rotation of the rotation hinge part 1710 relative to the base hinge part when the means 1750 for secure fixation is in an inactive position and to lock the rotation hinge part 1710 relative to the base hinge part when the means 1750 for secure fixation is in an active position. The means 1750 for secure fixation is configured to enable secure fixation of the rotating hinge part 1710 with respect to the base hinge part 1720 in at least one fixed angular position of the rotating hinge part 1710 with respect to the base hinge part 1720. Preferably, the means 1750 for secure fixation is located in the hinge space 1730. In a particular embodiment, to create the secure fixation of the rotating hinge part 1710 with respect to the base hinge part 1720 in at least one fixed angular position, the base hinge segment 1721 of the base hinge part 1720 comprises a base indentation 1723, and the hinge segment 1711 of the rotating hinge part 1710 comprises one or more rotating part indentations 1713, wherein the base indentation 1723 and the rotating part indentations 1713 are configured to receive a part of the hinge fixation means 1760 and wherein the simultaneous receiving of part of the hinge fixation means 1760 by the base indentation 1723 of the base hinge part 1720 and one of the rotating part indentations 1713 of the rotating hinge part 1710 results in the secure fixation of the rotating hinge part 1710 relative to the base hinge part 1720 in a fixed angular position. In a particular embodiment, the part of hinge fixation means 1760 which is receivable in the indentations is a dent 1754. Preferably, the hinge fixation means 1760 comprises the dent 1754. Preferably, the base indentation 1713 and the rotating part indentations 1723 are located inside the hinge space 1730. Preferably, the base and the rotating part indentations 1713, 1723 are U-shaped indentations, as illustrated in FIGS. 21-22, and the part of the hinge fixations means 1760 which is receivable in the indentations 1713, 1723, in particular the dent 1754, has a shape corresponding to the shape of the indentations. Accordingly, the embodiment where the indentations 1713, 1723 are U-shaped, the dent 1754 is also a U-shaped dent 1754, as illustrated in FIG. 22.

Within the context of the embodiment of FIG. 21, fixation in more than one fixed angular position is enabled by providing more than one rotating part indentations 1713 to create a medical fixation device 1001 wherein the rotating hinge part 1710 comprises more than one fixed angular position with respect to the base hinge part 1720. Preferably, the rotating hinge part 1710 comprises three or more rotating part indentations 1713.

In a particular embodiment, the rotating hinge part 1710 comprises three rotating part indentations 1713. In a preferred particular embodiment, as illustrated in FIG. 20, the three indentations 1713 enable secure fixation of the rotating hinge part 1710 in three fixed angular positions with respect to the base hinge part 1720: an up angular position 1791, a down angular position 1792 and a folded angular position 1790. The up angular position 1791 is a fixed angular position of 200° to 260°, preferably 210° to 250°, more preferably 220° to 240°. The down angular position 1792 is a fixed angular position of 130° to 175°, preferably 140° to 175°, more preferably 150° to 170°. The folded angular position 1490 is a fixed angular position of 175° to 185°, preferably 179° to 181°, more preferably 180°.

In another particular embodiment, the rotating hinge part 1710 comprises more than one rotating part indentations 1713 at equal distances from each other, such as every 30°, every 15°, every 10°, every 5° or every 1°. This enables a greater adaptability of the fixed angular position to a unique subject and surgery.

In a particular embodiment, the hinge fixation means 1760 is configured to perform an axial translation movement relative to the indentations 1713, 1723. This can be realized by any means to obtain one-dimensional translational movement known in the art. Preferably, the axial translation movement of the hinge fixation means 1760 relative to the indentations 1713, 1723 is a one-dimensional axial translation movement. Thus, the axial translational movement of the hinge fixation means 1760 away from the indentations 1713, 1723 enables rotational movement of the rotating hinge part 1710 with respect to the base hinge part 1720. Accordingly, the axial translational movement of the hinge fixation means 1760 towards and into the indentations 1713, 1723 results in the secure fixation of the rotating hinge part 1710 in an angular position with respect to the base hinge part 1720.

In a particular embodiment, the fixation mechanism, in particular the means 1750 for secure fixation, is configured to enable automatic secure fixation of the rotating hinge part 1710 in an angular position with respect to the base hinge part 1720, when the base indentation 1723 is aligned with one of the rotating part indentations 1713. In a particular embodiment, for example in FIGS. 21-22, the fixation mechanism, in particular the means 1750 for secure fixation, comprises a force element 1751 which creates a force on the hinge fixation means 1760 in the axial translation direction towards the indentations 1713, 1723 causing the automatic axial translation movement of the hinge fixation means 1760 into the indentations 1713, 1723. This results in automatic secure fixation of the rotating hinge part 1710 in an angular position with respect to the base hinge part 1720 by means of the hinge fixation means 1760, when the base indentation 1723 of the base hinge part 1720 is aligned with one of the rotating part indentations 1713 of the rotating hinge part 1710. Preferably, the force element 1751 is a mechanical force element, more preferably a spring.

Switching Between Rotatable Connection and Secure Fixation

In a particular embodiment, for example in FIGS. 21-22, the fixation mechanism, in particular the means 1750 for secure fixation comprises a button 1752, which is configured to enable switching between allowing rotatable connection of the first segment 1202 relative to the second segment 1203 of the second elongate element 1200, and securely fixing the first segment 1202 in at least one fixed angular position relative to the second segment 1203. Preferably, the second hinge 1700 comprises a button 1752, which is configured to enable switching between allowing the rotation of the rotating hinge part 1710 relative to the base hinge part 1720, and the secure fixation of the rotating hinge part 1710 relative to the base hinge part 1720 in at least one fixed angular position. This button 1752 enables easy and intuitive manipulation by the surgeon to quickly switch between rotational movement and secure fixation of the connection between the first segment 1202 and the second segment 1203, in particular the second hinge 1700 and thus to optimally position the medical fixation device for surgery with minimal effort. In a further particular embodiment, the hinge segment 1711 of the rotating hinge part 1710 and/or the base hinge segment 1721 of the base hinge part 1720 comprises a button opening 1725, which is configured to accommodate the button 1752 and to allow a user to press the button. In a preferred embodiment, the button 1752 is part of the hinge fixation means 1760 and is configured such that moving the button 1752 inwards causes the hinge fixation means 1760 to move in the axial translation direction out of the indentations 1713, 1723.

In a further particular embodiment, the means 1750 for secure fixation, in particular the hinge fixation means 1760, comprises an opening 1753, which is configured to accommodate the axis part 1740 when making the translation movement. In this way, the axis part 1740 passes through the hinge fixation means 1760 and helps guiding the movement.

In a further particular embodiment, as illustrated in FIG. 21, the axial translation movement of the hinge fixation means 1760 is realized by providing a button cover 1761 on one side of the hinge fixation means and a button base 1762 on the other side of the hinge fixation means 1760. The button cover 1761, the button base 1762 and the hinge fixation means 1750 are configured such that when assembled, the hinge fixation means 1760 can only move in one axial translation direction between the button cover 1761 and the button base 1762. In a further particular embodiment, the button cover 1761 and/or the button base 1762 comprise one or more guiding rails 1763, which are configured to prevent sideways movement of the hinge fixation means 1760. In a further particular embodiment, the button cover 1761 and/or the button base 1762 comprise one or more spring guides 1764, which are configured to guide the force element 1751, in particular the spring, when compressed and de-compressed in the axial translation direction. The spring guides 1764 may also be configured to create the end position of the hinge fixation means 1760 when moved away from the indentations 1713, 1723.

In a particular embodiment, as illustrated in FIG. 21, the button base 1762 is assembled to the base hinge segment 1721 of the base hinge part 1720 through one or more openings 1768. The second hinge 1700 comprises one or more fixation means 1767 to assemble the button base 1762 through the one or more openings 1768 in the button base 1762 and one or more corresponding openings 1727 in the base hinge segment 1721. Subsequently, once the button base 1762 is assembled, the hinge fixation means 1760 and force element 1751, in particular the spring, can be positioned in the button base 1762, and the button cover 1761 can be assembled over the hinge fixation means 1760. The button cover 1761 is assembled with one or more fixation means 1765 to the base hinge segment 1721 through the one or more openings 1766 in the button cover 1761 and one or more corresponding openings 1726 in the base hinge segment 1721. Alternatively, the button base 1762 and the button cover 1761 may be assembled to the hinge segment 1711 of the rotating hinge part 1710. Preferably, the fixation means 1765 and 1767 is a screw.

In a particular embodiment, as illustrated in FIG. 21, the hinge segment 1711 of the rotating hinge part 1710 is configured to assemble a slider 1770, which is configured to smoothly guide the rotation movement of the rotating hinge part 1710 with respect to the button cover 1761. In a further particular embodiment, the slider 1770 comprises one or more openings 1772 to be assembled with fixation means 1771. The fixation means 1771 securely fixes the slider 1770 to the hinge segment 1711 of the rotating hinge part 1710 through one or more openings 1772 in the slider 1770, and one or more corresponding openings 1717 in the hinge segment 1711.

In a preferred embodiment, the means 1750 for secure fixation comprises the hinge fixation means 1760, the button cover 1761 and the button base 1762. In a further preferred embodiment, the hinge fixation means 1760 comprises the button 1752, the opening 1753 and the dent 1754. In further preferred embodiment, the base hinge segment 1721 of the base hinge part 1720 comprises the hinge fixation means 1760, the button cover 1761 and the button base 1762.

The Connection Segments

The connection segment 1712 of the rotating hinge part 1710 and the base connection segment 1722 of the base hinge part 1720 are configured to be connected to and securely fixed to either the bar 1600 of the second elongate element 1200 or the base element 1300.

In a particular embodiment, the connection segment 1712 of the rotating hinge part 1710 is configured to be connected to and securely fixed to the bar 1600 of the second elongate element 1200, and the base connection segment 1722 of the base hinge part 1720 is configured to be connected to and securely fixed to the base element 1300.

In another particular embodiment, the connection segment 1712 of the rotating hinge part 1710 is configured to be connected to and securely fixed to the base element 1300, and the base connection segment 1722 of the base hinge part 1720 is configured to be connected to and securely fixed to the bar 1600 of the second elongate element 1200.

In a particular embodiment, for example in FIGS. 21-22, the connection segment 1712 comprises a tube 1718 and the base connection segment 1722 comprises a tube 1728. Each of the tubes 1718, 1728 may be a cylindrical tube or a polygonal tube, preferably a cylindrical tube or a rectangular tube, more preferably a cylindrical tube. Preferably, each of the tubes 1718, 1728 is a solid tube. Alternatively, one or both of the tubes 1718, 1728 is a hollow tube.

In a further particular embodiment, for example in FIGS. 21-22, the connection segment 1712, in particular the tube 1718, comprises one or more openings 1719, and the connection segment 1722, in particular the tube 1728, comprises one or more openings 1729. Depending on the component to which the respective connection segments 1712, 1722 are fixed, the openings 1719, 1729 are configured to accommodate either the means 1607 for secure fixation to the bar 1600 of the second elongate element 1200, or the means 1305 for secure fixation to the base element 1300.

The Base Element

Figure 23:
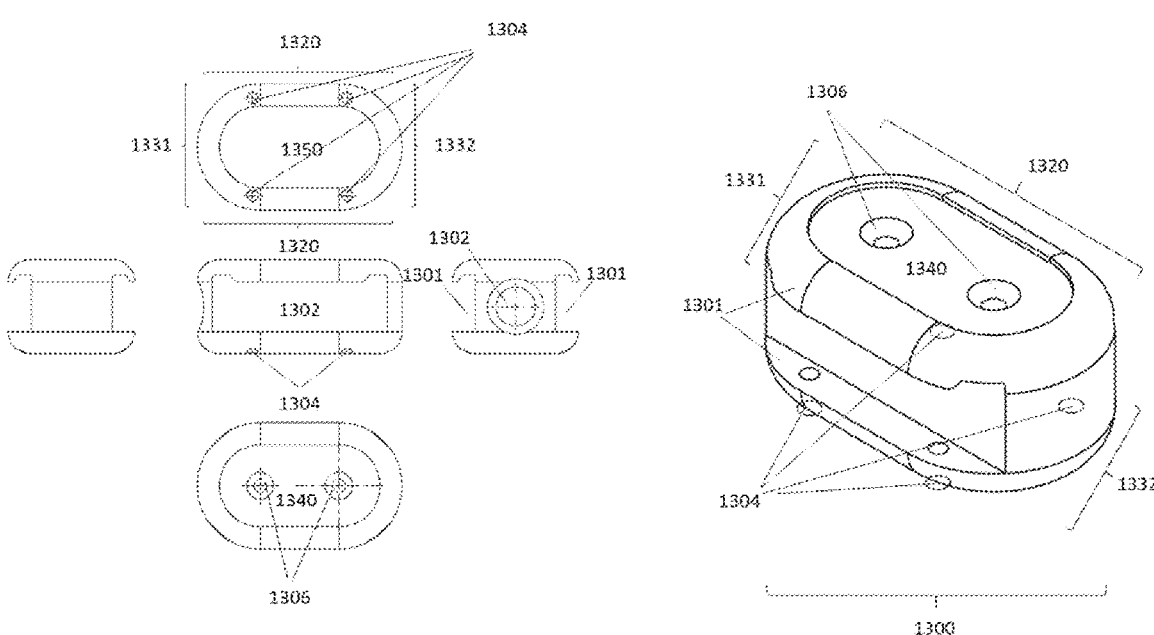
FIG. 23 illustrates the base element 1300 according to the alternative embodiment.

By way of illustration and not limited thereto, embodiments of standard and optional components of the base element 1300, are depicted in FIG. 23. The base element 1300 is configured to be connected to the operating table 502 and comprises a means 1303 for secure fixation of the base element to the operating table. For the purpose of the current invention, the base element 1300 would typically have a length of 80 mm to 250 mm, preferably 100 mm to 200 mm, more preferably 100 mm to 130 mm. The base element would typically have a width of 60 mm to 100 mm, preferably 70 mm to 90 mm, more preferably 75 mm to 85 mm. The base element 1300 would typically have a height of 40 mm to 80 mm, preferably 50 mm to 70 mm, more preferably 55 mm to 65 mm. These dimensions allow for secure and stable fixation of the base element 1300 to an operating table 502 and of the entire medical fixation device 1001 onto the operating table 502.

Figure 24:
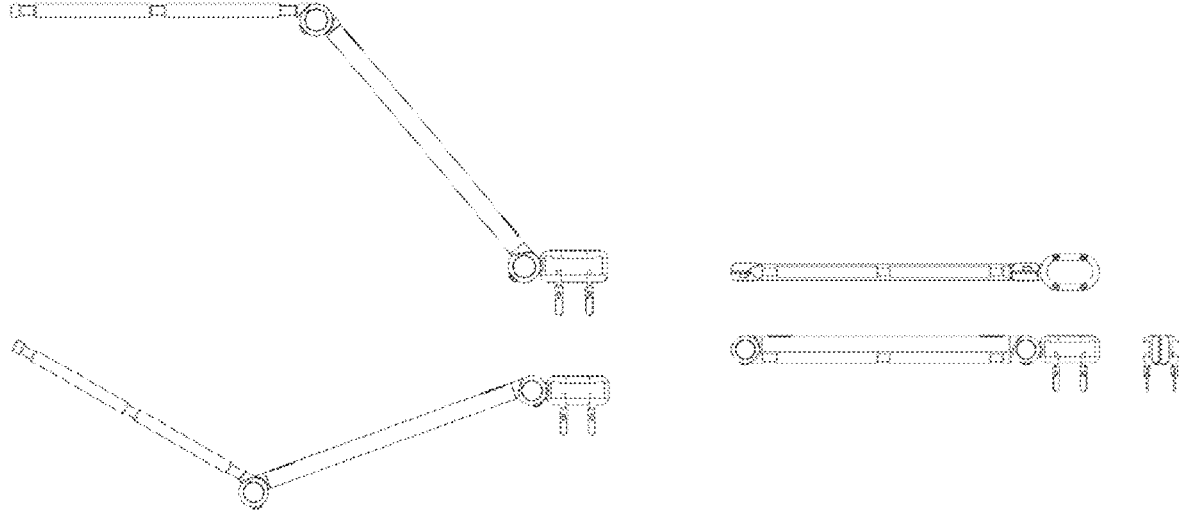
FIG. 24 illustrates the different configurations of the medical fixation device according to the alternative embodiment, comprising a base element 1300 with two clamps (1301)
Figure 25:
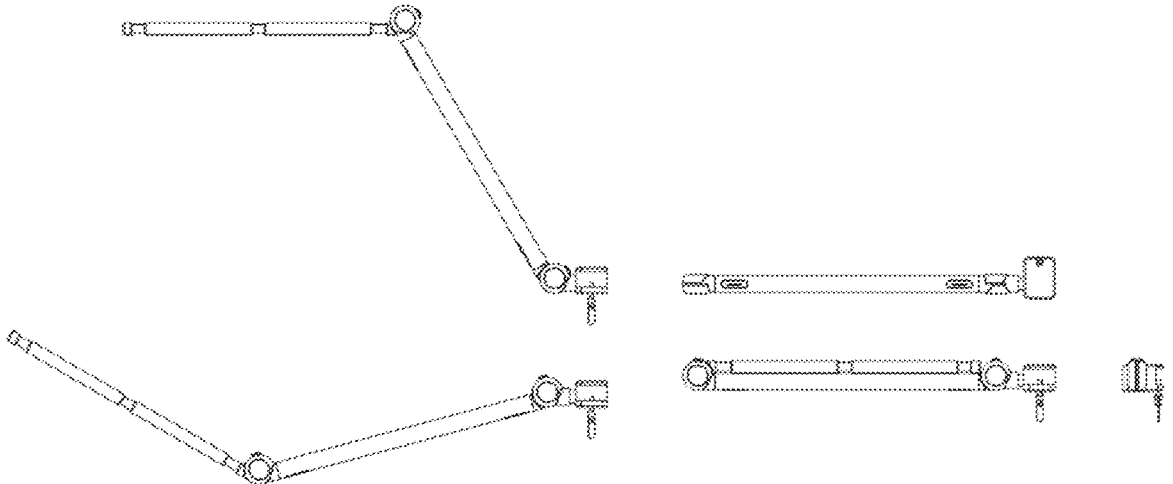
FIG. 25 illustrates the different configurations of the medical fixation device according to the alternative embodiment, comprising a base element 1300 with one clamp (1301)

In a particular embodiment, the base element 1300 comprises one or more clamps 1301, which are configured to be connected and securely fixated to the operating table 502. In a particular embodiment, the base element 1300 comprises one clamp 1301, as shown in FIG. 25. The one clamp 1301 can be a left-sided clamp or a right-sided clamp 1301, resulting in a left-sided or a right-sided medical fixation device 1001 respectively. This side-specific design of the base element 1300 and the corresponding medical fixation device 1001, enables positioning of the medical fixation device further away from the edge of the operating table, which provides more space on the operating table. In another particular embodiment, the base element 1300 comprises two clamps 1301, in particular one clamp 1301 on each of the two opposite long sides 1320 of the base element, as shown in FIGS. 23-24. The presence of a clamp on each long side 1320 of the base element 1300 facilitates convenient use of the medical fixation device 1001 on both sides of the operating table 502. Preferably, the one or more clamps 1300 comprise a means 1303 for secure fixation of the clamps to the operating table. In a particular embodiment, the one or more clamps 1301 are configured to be releasably connected to the operating table 502, in particular to the rail of the operating table. In a further particular embodiment, the one or more clamps 1301 comprise one or more screws 1303, preferably one or two screws, in one or more corresponding openings 1304 for secure fixation of the clamp to the operating table, as illustrated in FIG. 23. Preferably, the openings 1304 are located at the bottom 1350 of the base element 1300. The various types of screws suitable for secure fixation of the clamp to the operating table are known to those skilled in the art, and comprise but are not limited to, wing screws, shelf screws, bolts etc.

In a particular embodiment, shown in FIG. 23, the base element 1300 comprises two clamps 1301, in particular one clamp 1301 on each of the two opposite long sides 1320 of the base element. Preferably, the two clamps 1301 are identical. In a further particular embodiment, each clamp 1301 comprises two means 1303 for secure fixation of the clamp to the operating table. Preferably, the means for secure fixation 1303 comprises screws. In a further particular embodiment, each of the clamps comprises two openings 1304, which are configured to accommodate the means 1303 for secure fixation. In a further particular embodiment, the distance between the two openings 1304 in each clamp is 40 mm to 80 mm, preferably 50 mm to 70 mm, more preferably 55 mm to 65 mm.

The two short sides of the base element are also referred to as the first end 1331 and the second end 1332

The base element 1300 is configured to be connected to the second elongate element 1200, in particular the second segment 1203 of the second elongate element 1200, more in particular one of the connection segments 1712, 1722 of the second hinge 1700. Preferably, the base element 1300 comprises a cavity 1302, which is configured to receive a part of the second elongate element 1200, in particular a part of the second segment 1203 of the second elongate element 1200, more in particular one of the connection segments 1712, 1722 of the second hinge 1700. Preferably, the said cavity 1302 is located at the first end 1331 of the base element 1300. In a preferred embodiment, the cavity 1302 of the base element 1300 is a cylindric cavity. In an alternative embodiment, the cavity 1302 of the base element 1300 is a polygonal cavity. Examples of polygonal cavities are analogous to those described for the cavities 1604, 1605 of the bar 1600 of the second elongate element 1200. In another preferred embodiment, the cavity 1302 of the base element 1300 is a rectangular cavity.

Furthermore, the base element 1300 comprises a means 1305 for secure fixation of the second elongate element 1200 to the base element 1300. In a preferred embodiment, the fixation means 1305 is analogous to the means 1607 of the bar 1600 of the second elongate element 1200. In a particular embodiment the base element 1300 comprises one or more openings 1306 wherein the openings 1306 are configured to accommodate the means 1305 for secure fixation of the second connection part 1700 to the base element 1300. Preferably, the base element 1300 comprises two or more openings 1306 on top 1340 of the base element. Preferably, the openings 1306 are aligned in line with the long axis of the base element 1300.

In a particular embodiment, shown in FIG. 23, the base element 1300 comprises two openings 1306 at the top 1340 of the base element, wherein the openings 1306 are aligned in line with the long axis of the base element 1300. In a further particular embodiment, the distance between the two openings 1306 of the base element 1300 is 30 mm to 70 mm, preferably 40 mm to 60 mm, more preferably 45 mm to 55 mm.

Materials

For the purpose of the current invention, the described elements (the first elongate element 100, 1100, the extension element 150, the second elongate element 200, 1200, the base element 300, 1300, the connection part 400, 1400, the second hinge 1700) would need to be manufactured from rigid and resilient material, such that these elements remain intact and preserve their position under the forces exerted on the medical fixation device by the surgical instruments. Furthermore, the materials of the medical fixation device should be able to withstand conventional cleaning conditions. In a particular embodiment, the described elements are made of a metal. The metal may comprise, but is not limited to carbon steel, stainless steel, aluminum, titanium, or any other metal which is suitable for manufacturing of medical devices for use in surgery. In a preferred embodiment, the described elements are made of aluminum and/or stainless steel. The described elements may also be made from a resilient composite material, such as a carbon fiber composite, or from a rigid thermoplastic material such as polyoxymethylene or polyaryletherketone. In another preferred embodiment, the described elements are made of aluminum, stainless steel and/or polyoxymethylene. Different elements may be made of different materials.

Where necessary, other materials may also be used for the manufacture of the medical fixation device, such as plastic, rubber, silicone, other metals, resins, polymers, and other materials which are suitable for the manufacture of medical devices.

Configurations

As illustrated in FIG. 10, the rotatable connection of the first elongate element 100, 1100 with respect to the second elongate element 200, 1200 enables convenient folding and unfolding of the medical fixation device 001, 1001. The foldable design facilitates transportation and storage of the device, while simultaneously enabling easy assembly. The structure of the foldable design realized by the specific structure of the connection between the first elongate element 100, 1100 and the second elongate element 200, 1200, in particular connection part 400, 1400 provides a foldable structure which provides, after secure fixation in the predefined angle, a very robust medical fixation device that preserves its position under the forces exerted on the medical fixation device by surgical instruments.

In the alternative embodiment of the medical fixation device 1001, the second hinge 1700 of the second elongate element 1200 enables an even more compact folded configuration. FIG. 24 illustrates two examples of the unfolded configurations (on the left) and the folded configuration (on the right) of the medical fixation device 1001.

In the unfolded configuration, the medical fixation device 001 would typically span over a horizontal distance of 900 mm to 1300 mm, preferably 1000 mm to 1200 mm, more preferably 1110 mm to 1130 mm, and over a vertical distance of 250 mm to 500 mm, preferably 300 mm to 450 mm, more preferably 310 mm to 420 mm.

In a particular embodiment as illustrated in FIG. 10, in the folded configuration, the first elongate element 100, 1100 may be locked onto the second elongate element 200, 1200. This locking prevents unexpected unfolding of the device, thereby increasing the safety and the convenience of use of the medical fixation device. For example, the first elongate element 100, 1100 can be locked onto the second elongate element 200, 1200 using a clamp 204.

Stiffness and Strength

The medical fixation device 001 according to the invention is designed and manufactured such that, when connected to an operating table as illustrated in FIG. 11, it remains intact and maintains its position when forces are exerted thereon by the surgical instruments 600, such as surgical retractors 500. In view of the design of the medical fixation device 1, the surgical instruments 600 will primarily exert forces onto the first elongate element 100, in particular on the connection members 104 of the first elongate element, as illustrated in FIG. 11. The forces exerted onto the first elongate element 100 will be transferred onto the other parts of the medical fixation device, and accumulate in the connection between the first elongate element 100 and the second elongate element 200, in particular the connection part 400, and in the base element 300.

For the purpose of the current invention, the first elongate element 100, in particular the first end 102 of the first elongate element, would typically displace by less than 10 mm, preferably less than 7 mm, more preferably less than 5 mm when forces of 90 N, in particular horizontal or vertical transversal forces, are exerted thereon by the surgical instruments, such as surgical retractors. In practice, displacement of a medical fixation device by less than 10 mm would not be disturbing or distracting for the surgeon, in particular during orthopedic surgeries, more in particular during shoulder surgeries. In practice, the ability to withstand transversal forces of up to 90 N means that even if the medical fixation device, in particular the first elongate element, was to carry the weight of an entire patient's arm (on average 3.5 kg and 5.5 kg for females and males respectively) or to withstand some forces exerted by a surgeon or a surgical assistant touching or leaning on the device, the medical fixation device would maintain its position with only a minimal displacement of the first elongate element and no displacement of the other elements.

Likewise, in the alternative embodiment, the first elongate element 1100, in particular the first end 1102 of the first elongate element, would typically displace by less than 10 mm, preferably less than 7 mm, more preferably less than 5 mm when forces of 90 N, in particular horizontal or vertical transversal forces, are exerted thereon by the surgical instruments, such as surgical retractors.

Sterile Use

It is the common surgical practice to operate in sterile environment. Therefore, medical devices used during surgery are typically covered with a sterile cover.

In a particular embodiment, the medical fixation device 001, 1001 is covered with a sterile cover during surgery. The sterile cover may be a surgical drape, a sterile sleeve or any other sterile cover which is suitable for sterile covering an elongated medical device. In a further particular embodiment, the medical fixation device is covered with surgical drape during surgery. In another particular embodiment, the medical fixation device is covered with a sterile sleeve, in particular a sterile sleeve with dimensions and shape corresponding to the dimensions and shape of the medical fixation device. In a further particular embodiment, the sterile sleeve is transparent.

Medical Device Set

The medical fixation device according to embodiments of the present invention may be provided as a single component, or may be provided from a variety of separate components which together form a set of parts.

Figure 12:
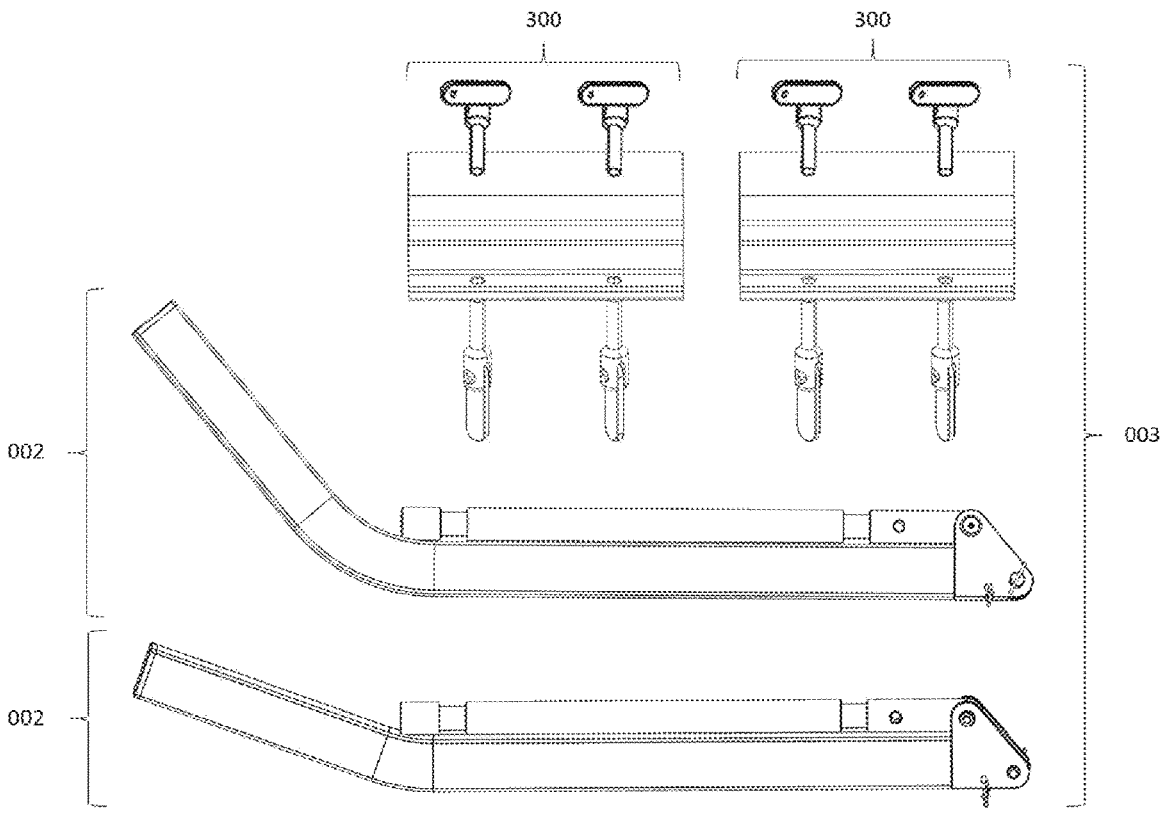
FIG. 12 illustrates a medical device set 003, comprising two base elements 300 (on the top) and two folded medical fixation bars 002, a high-type medical fixation bar (in the middle) and a low-type medical fixation bar (on the bottom)

In an aspect of the present invention, the invention relates to a medical device set 003 comprising one or more medical fixation devices 001. In a particular embodiment, the medical device set comprises one or more medical fixation bars 002 and one or more base elements 300. Preferably, the medical device set 003 comprises medical fixation bars 002 in the folded configuration. In a further particular embodiment, the medical device set comprises two medical fixation bars and two base elements. In a preferred embodiment, the medical device set comprises one high-type medical fixation bar, one low-type medical fixation bar and two base elements, as illustrated in FIG. 12.

In an alternative embodiment, the medical device set 003 comprises one or more medical fixation devices 1001. The medical fixation devices 1001 are assembled. Preferably, the medical device set 003 comprises medical fixation devices 1001 in the folded configuration, which is illustrated in FIG. 24 (on the left). In a further alternative embodiment, the medical device set 003 comprises two medical fixation devices 1001. In a further alternative embodiment, the medical device set 003 comprises one left-sided medical fixation device and one right-sided medical fixation device. As illustrated in FIGS. 24-25, each of the two medical fixation devices 1001 can be unfolded into a high configuration (on the left, top) and a low configuration (on the left, bottom). Whether the medical fixation device 1001 is side-specific (FIG. 25) or not side-specific (FIG. 24) depends on the base element design 1300, as described above. Typically, the medical fixation devices comprised in one medical device set will be placed in one package. The package may be a wrapping, a box, a container or any other type of package which is suitable for packaging of medical devices.

Medical Device System

In another aspect of the present invention, the invention relates to a medical device system for keeping open a wound during surgery, wherein at least one of the components is a medical fixation device. The other components may for example be surgical instruments, such as surgical retractors, or a surgical drape.

Surgery

In a further aspect of the present invention, the invention relates to a medical fixation device, a medical device set or a medical device system for use in surgery.

Embodiments of the present invention can be used in various types of surgery. The various types of surgery are known to those skilled in the art, and comprise but are not limited to, orthopedic surgery, trauma surgery, neurosurgery, plastic and reconstructive surgery, thoracic surgery, abdominal surgery, cardiovascular surgery, urological surgery, gynaecological surgery, otolaryngological and head and neck surgery, oral and maxillofacial surgery, eye surgery, etc. Orthopedic surgery comprises but is not limited to arm, leg and spine surgery. Arm surgery comprises, but is not limited to, shoulder surgery, upper arm surgery, lower arm surgery or hand surgery. Leg surgery comprises but is not limited to, hip surgery, upper leg surgery, lower leg surgery or foot surgery. Shoulder surgery comprises but is not limited to, total shoulder arthroplasty (including reverse total shoulder arthroplasty), shoulder trauma surgery (including fracture reposition), rotator cuff repair, repair of the shoulder joint (e.g. labral repair). In a particular embodiment, the present invention concerns a medical fixation device for use in orthopedic surgery. In a preferred embodiment, the orthopedic surgery is arm surgery, preferably shoulder surgery, more preferably total shoulder arthroplasty or shoulder trauma surgery.

Embodiments of the present invention can be used in various surgical positions. The various surgical positions are known to those skilled in the art, and comprise but are not limited to, supine position, beach chair position (i.e. sitting or semi-sitting position), prone or semi-prone position, lateral position, lithotomy position, Trendelenburg's Position, reverse Trendelenburg's Position, Jackknife position, etc. In a particular embodiment, the present invention concerns a medical fixation device for use in beach chair position.

In a preferred embodiment, the present invention concerns a medical fixation device for use in shoulder surgery, which is performed in beach chair position.

In another preferred embodiment, the present invention concerns a medical device set for use in shoulder surgery. Preferably, the shoulder surgery is performed in beach chair position. In a further preferred embodiment the medical device set for use in shoulder surgery comprises one high-type medical fixation bar 002, one low-type medical fixation bar 002 and two base elements 300. In an alternative preferred embodiment the medical device set for use in shoulder surgery comprises two medical fixation devices 1001.

In yet another preferred embodiment, the present invention concerns a medical device system for use in shoulder surgery. Preferably, the shoulder surgery is performed in beach chair position. In a further preferred embodiment, the medical device system comprises one high-type medical fixation bar, one low-type medical fixation bar, two base elements and two or more surgical instruments. In another further preferred embodiment, the medical device system comprises one high-type medical fixation bar, one low-type medical fixation bar, two base elements and one or more surgical drape. In a yet another further preferred embodiment, the medical device system comprises one high-type medical fixation bar, one low-type medical fixation bar, two base elements, one or more surgical retractors and one or more surgical drape.

In an alternative preferred embodiment the medical device system for use in shoulder surgery, which is performed in beach chair position comprises two medical fixation devices 1001, or two medical fixation devices 1001 and one or more surgical instruments, or two medical fixation devices 1001 and one or more surgical drapes, or two medical fixation devices 1001 and one or more surgical instruments and one or more surgical drapes.

Embodiments of the present invention can furthermore be used for different types of patients, such as for example less muscular or more muscular, shorter or taller, skinnier or larger patients.

Method for Installation

In a further aspect of the present invention, the invention relates to a method for installation of the described medical fixation device, medical device set or medical device system.

Method of Installation of the Medical Fixation Device

In a particular embodiment, the present invention relates to a method for installation of the described medical fixation device, the method comprising the steps of:

connecting the base element 300 to the side of the operating table 502;

securely fixing the base element 300 to the side of the operating table 502;

connecting the medical fixation bar 002 to the base element 300;

securely fixing the medical fixation bar 002 to the base element 300.

The medical fixation bar 002 may be the high-type medical fixation bar or the low-type medical fixation bar. If applicable, the medical fixation bar 002 may be slid into the base element 300 in the up-orientation or in the down-orientation. It is an advantage of the described installation method that the medical fixation device can be installed in a very easy and intuitive manner, and is straight-forward for new users.

In a further particular embodiment, the present invention relates to a method for installation of the described medical fixation device, the method comprising the steps of:

connecting the base element 300 to the side of the operating table 502;

securely fixing the base element 300 to the side of the operating table 502;

connecting the folded medical fixation bar 002 to the base element 300, in particular, sliding the folded medical fixation bar 002 into the base element 300;

securely fixing the folded medical fixation bar 002 to the base element 300;

unfolding the medical fixation bar 002 by rotating the first elongate element 100 away from the second elongate element 200 until the maximal possible angle, also referred to as the fixed angle.

In a further particular embodiment, the present invention relates to a method for installation of the described medical fixation device, the method comprising the steps of:

connecting the base element 300 to the side of the operating table 502;

securely fixing the base element 300 to the side of the operating table 502;

connecting the folded medical fixation bar 002 to the base element 300, in particular, sliding the folded medical fixation bar 002 into the base element 300;

securely fixing the folded medical fixation bar 002 to the base element 300;

disconnecting the secure fixation means 406 or the secure fixation between the first elongate element 100 and the second elongate element 200, in particular, removing the safety pin 406 from the connection part 400 of the medical fixation bar 002;

unfolding the medical fixation bar 002 by rotating the first elongate element 100 away from the second elongate element 200 until the maximal possible angle, also referred to as the fixed angle;

connecting the secure fixation means 406 or the secure fixation between the first elongate element 100 and the second elongate element 200 to securely fix the first elongate element 100 at a fixed angle with respect to the second elongate element 200, in particular, inserting the safety pin 406 into the connection part 400.

In an alternative embodiment, the present invention relates to a method for installation of the described medical fixation device 1001, the method comprising the steps of:

connecting the base element 1300 to the side of the operating table 502;

securely fixing the base element 1300 to the side of the operating table 502;

unfolding the medical fixation device 1001 by rotating the first hinge 1400 and the second hinge 1700 until the selected fixed angular position and securely fixing the hinges in that angular position.

Method of Installation of the Medical Device Set

In another particular embodiment, the present invention relates to a method for installation of the described medical device set comprising one or more medical fixation devices.

In this case, the steps of the method for installation of the medical fixation device are repeated for each medical fixation device present in the medical device set.

In a particular embodiment, the present invention relates to a method for installation of the described medical device set, the method comprising the steps of:

connecting the base element 300 to the side of the operating table 502;

securely fixing the base element 300 to the side of the operating table 502;

connecting the medical fixation bar 002 to the base element 300;

securely fixing the medical fixation bar 002 to the base element 300;

for each medical fixation device 001 of the medical fixation device set 003.

In an alternative embodiment, the present invention relates to a method for installation of the described medical fixation device 1001, the method comprising the steps of:

connecting the base element 1300 to the side of the
operating table 502;
securely fixing the base element 1300 to the side of the
operating table 502;
unfolding the medical fixation device 1001 by rotating the
first hinge 1400 and optionally the second hinge 1700
until the selected fixed angular position and securely
fixing the hinges in that angular position;
for each medical fixation device 1001 of the medical fixation
device set 003.

In a preferred embodiment, the present invention relates
to a method for installation of the medical device set for use
in shoulder surgery comprising one high-type medical fixa-
tion bar, one low-type medical fixation bar and two base
elements. In this case, the high-type medical fixation bar is
preferably placed in the up-orientation on the opposite side
of the operated shoulder (contralateral side), and the low-
type medical fixation bar is preferably placed in the down-
orientation of the side of the operated shoulder (ipsilateral
side). This means that if the patient undergoes surgery of the
right shoulder, the high-type medical fixation bar is prefer-
ably placed in the up-orientation on the left side of the
patient, and the low-type medical fixation bar is preferably
placed in the down-orientation of right the side of the
patient, as illustrated in FIG. 11. Such installation would
maximize accessibility of the surgical site for the surgeon,
and simultaneously enable optimal expansion of the edges of
the incision by the surgical retractors connected to the
described medical fixation devices.

Likewise, in a preferred alternative embodiment, the
present invention relates to a method for installation of the
medical device set for use in shoulder surgery comprising
two medical fixation devices 1001. In this case, one medical
fixation device 1001 is preferably placed in the high con-
figuration on the opposite side of the operated shoulder
(contralateral side), and one medical fixation device 1001 is
preferably placed in the low configuration of the side of the
operated shoulder (ipsilateral side).

Method of Installation of the Medical Device System

In yet another particular embodiment, the present inven-
tion relates to a method for installation of the described
medical device system.

In this case, firstly, the steps of the method for installation
of the medical fixation device are repeated for each medical
fixation device comprised in the medical device system.

(optionally) Secondly, the one or more medical fixation
devices are covered with one or more sterile covers. Pref-
erably, the sterile cover is a surgical drape or a sterile sleeve.

(optionally) Thirdly, one or more surgical instruments are
connected to the one or more medical fixation devices.

In a preferred embodiment, the present invention relates
to a method for installation of the medical device system
comprising one high-type medical fixation bar, one low-type
medical fixation bar, two base elements, one or more sur-
gical instruments, such as retractors, and one or more
surgical drapes.

In an alternative preferred embodiment, the present inven-
tion relates to a method for installation of the medical device
system comprising two medical fixation devices 1001, one
or more surgical instruments, such as retractors, and one or
more surgical drapes.

The invention claimed is:
1. A medical fixation device (001, 1001) for connecting
one or more surgical instruments (600) such as retractor
devices (500) to an operating table (502) in the space around
the operating table (503), the medical fixation device com-
prising:

42 two elongate elements, a first elongate element (100,
1100) and a second elongate element (200, 1200),
a connection part (400, 1400) for connecting the first
elongate element (100, 1100) to the second elongate
element (200, 1200),
a fixation mechanism configured (406, 1450) for secure
fixation of the first elongate element (100, 1100) in at
least one fixed angular position relative to the second
elongate element (200, 1200),
a base element (300, 1300) connected to the second
elongate element (200, 1200) and configured to be
connected to the operating table (502),
one or more first screws (305, 1305) for secure fixation of
the second elongate element (200, 1200) to the base
element (300, 1300), and
one or more second screws (303, 1303) for secure fixation
of the base element (300, 1300) to the operating table
(502),
wherein the first elongate element (100, 1100) is config-
ured to be releasably connected to one or more, pref-
erably two or more, more preferably three or more,
surgical instruments (600),
wherein the connection part (400, 1400) is configured to
allow rotatable connection of the first elongate element
(100, 1100) relative to the second elongate element
(200, 1200) when the fixation mechanism configured
(406, 1450) for the secure fixation is not connected, and
wherein the connection part (400, 1400) is configured
to enable secure fixation of the first elongate element
(100, 1100) in at least one fixed angular position
relative to the second elongate element (200, 1200)
when the fixation mechanism configured (406, 1450)
for the secure fixation is connected.

2. A medical fixation device (001, 1001) according to
claim 1, wherein the first elongate element (100, 1100)
comprises two or more connection members (104, 1104),
each of which configured to be releasably connected to one
or more surgical instruments (600).

3. A medical fixation device (001, 1001) according to
claim 1, wherein the connection part (400, 1400) is config-
ured to allow rotatable connection of the first elongate
element (100, 1100) relative to the second elongate element
(200, 1200) at an angular position selectable from 0° up to
360°.

4. A medical fixation device (001, 1001) according to
claim 1, wherein the connection part (400, 1400) and the
fixation mechanism configured (406, 1450) for secure fixa-
tion of the first elongate element (100, 1100) in at least one
fixed angular position relative to the second elongate ele-
ment (200, 1200), are configured to enable secure fixation of
the first elongate element (100, 1100) in more than one fixed
angular position relative to the second elongate element
(200, 1200) at an angular position selectable from 0° up to
360°, such as every 30°, every 15°, every 10°, every 5° or
every 1°.

5. A medical fixation device (001, 1001) according to
claim 1, wherein the fixation mechanism configured (1450)
for secure fixation of the first elongate element (100, 1100)
in at least one fixed angular position relative to the second
elongate element (200, 1200) is configured to enable auto-
matic secure fixation when the first elongate element (100,
1100) reaches a selected fixed angular position relative to the
second elongate element (200, 1200).

6. A medical fixation device (001, 1001) according to
claim 1, wherein the fixation mechanism configured (1450)
for secure fixation of the first elongate element (100, 1100)
in at least one fixed angular position relative to the second elongate element (200, 1200) comprises a button (1452), which is configured to enable switching between allowing rotatable connection of the first elongate element (100, 1100) relative to the second elongate element (200, 1200), and securely fixing the first elongate element (100, 1100) in at least one fixed angular position relative to the second elongate element (200, 1200).

7. A medical fixation device (001, 1001) according to claim 1, wherein the connection part (400, 1400) is a first hinge (1400) that comprises a rotating hinge part (1410) and a base hinge part (1420), wherein the rotating hinge part (1410) and the base hinge part (1420) are configured to allow rotatable connection of the rotating hinge part (1410) relative to the base hinge part (1420) when the fixation mechanism (1450) for the secure fixation of the first elongate element (100, 1100) in at least one fixed angular position relative to the second elongate element (200, 1200) is not connected, and to enable secure fixation of the rotating hinge part (1410) in at least one fixed angular position relative to the base hinge part (1420) when the fixation mechanism configured (1450) for the secure fixation of the first elongate element (100, 1100) in at least one fixed angular position relative to the second elongate element (200, 1200) is connected, and wherein the rotating hinge part (1410) and the base hinge part (1420) are configured for connecting the first hinge (1400) to respectively the first elongate element (1100) and the second elongate element (1200).

8. A medical fixation device (001, 1001) according to claim 1, wherein the fixation mechanism configured (406, 1450) for secure fixation of the first elongate element (100, 1100) in at least one fixed angular position relative to the second elongate element (200, 1200) is part of the connection part (400, 1400).

9. A medical fixation device (001, 1001) according to claim 1, wherein the second elongate element (200, 1200) comprises a first segment (202, 1202) and a second segment (203, 1203), wherein the first segment (202, 1202) is at a fixed angle with respect to the second segment (203, 1203) and wherein the second elongate element (200, 1200) comprises a fixation mechanism configured (1750) for secure fixation of the first segment (1202) at a fixed angular position with respect to the second segment (1203).

10. A medical fixation device (001, 1001) according to claim 1, wherein the second elongate element (200, 1200) comprises a first segment (202, 1202) and a second segment (203, 1203), wherein the first segment (202, 1202) is at a fixed angle with respect to the second segment (203, 1203) and wherein the second elongate element (200, 1200) comprises a fixation mechanism configured (1750) for secure fixation of the first segment (1202) at a fixed angular position with respect to the second segment (1203), and wherein the fixation mechanism (1750) for secure fixation of the second elongate element (200, 1200) is configured to enable automatic secure fixation when the first segment (1202) reaches a selected fixed angular position relative to the second segment (1203).

11. A medical fixation device (001, 1001) according to claim 1, wherein the second elongate element (200, 1200) comprises a first segment (202, 1202) and a second segment (203, 1203), wherein the first segment (202, 1202) is at a fixed angle with respect to the second segment (203, 1203) and wherein the second elongate element (200, 1200) comprises a fixation mechanism configured (1750) for secure fixation of the first segment (1202) at a fixed angular position with respect to the second segment (1203), and wherein the fixation mechanism configured (1750) for secure fixation of the second elongate element (200, 1200) comprises a button (1752), which is configured to enable switching between allowing rotatable connection of the first segment (1202) relative to the second segment (1203), and securely fixing the first segment (1202) in at least one fixed angular position relative to the second segment (1203).

12. A medical fixation device (001, 1001) according to claim 1, wherein the second elongate element (200, 1200) comprises a bar (1600) and a second hinge (1700), wherein the bar (1600) and a part of the second hinge (1700) form a first segment (1202), and another part of the second hinge (1700) forms a second segment (1203), and wherein the second hinge (1700) is configured to change the fixed angle between one or more fixed angular positions, causing that the first segment (1202) is at a fixed angular position with respect to the second segment (1203).

13. A medical fixation device (001, 1001) according to claim 1, wherein the second elongate element (200, 1200) comprises a bar (1600) and a second hinge (1700), wherein the bar (1600) and a part of the second hinge (1700) form a first segment (1202), and another part of the second hinge (1700) forms a second segment (1203), and wherein the second hinge (1700) is configured to change the fixed angle between one or more fixed angular positions, causing that the first segment (1202) is at a fixed angular position with respect to the second segment (1203), and wherein the second hinge (1700) of the second elongate element (200, 1200) is configured to enable secure fixation of the first segment (1202) in more than one fixed angular position relative to the second segment (1203) at an angular position selectable from 0° up to 360°, such as every 30°, every 15°, every 10°, every 5° or every 1°.

14. A medical fixation device (001, 1001) according to claim 1, wherein the second elongate element (200, 1200) comprises a bar (1600) and a second hinge (1700), wherein the bar (1600) and a part of the second hinge (1700) form a first segment (1202), and another part of the second hinge (1700) forms a second segment (1203), and wherein the second hinge (1700) is configured to change the fixed angle between one or more fixed angular positions, causing that the first segment (1202) is at a fixed angular position with respect to the second segment (1203), and wherein the second hinge (1700) of the second elongate element (200, 1200) is configured to allow rotatable connection of the first segment (1202) relative to the second segment (1203) when the fixation mechanism configured (1750) for the secure fixation of the first segment (1202) at a fixed angular position with respect to the second segment (1203) is not connected, and to enable secure fixation of first segment (1202) in at least one fixed angular position relative to the second segment (1203) when the fixation mechanism configured (1750) for the secure fixation of the first segment (1202) at a fixed angular position with respect to the second segment (1203) is connected.

15. A medical fixation device (001, 1001) according to claim 1, wherein the second elongate element (200, 1200) comprises a bar (1600) and a second hinge (1700), wherein the bar (1600) and a part of the second hinge (1700) form a first segment (1202), and another part of the second hinge (1700) forms a second segment (1203), and wherein the second hinge (1700) is configured to change the fixed angle between one or more fixed angular positions, causing that the first segment (1202) is at a fixed angular position with respect to the second segment (1203), and wherein the second hinge (1700) comprises a rotating hinge part (1710) and a base hinge part (1720), wherein the rotating hinge part (1710) and the base hinge part (1720) are configured to allow rotatable connection of the rotating hinge part (1710) relative to the base hinge part (1720) when the fixation mechanism configured (1750) for the secure fixation of the first segment (1202) at a fixed angular position with respect to the second segment (1203) is not connected, and to enable secure fixation of the rotating hinge part (1710) in at least one fixed angular position relative to the base hinge part (1720) when the fixation mechanism configured (1750) for the secure fixation of the first segment (1202) at a fixed angular position with respect to the second segment (1203) is connected, and wherein the rotating hinge part (1710) and the base hinge part (1720) are configured for connecting the second hinge (1700) to respectively the base element (1300) and the bar (1600) of the second elongate element (1200).

16. A medical fixation device (001, 1001) according to claim 1, wherein the base element (300, 1300) comprises a cavity (302, 1302) which is configured to receive a part of the second elongate element (200, 1200) and which is configured to receive the one or more first screws (305, 1305) for secure fixation of the second elongate element (200, 1200) to the base element (300, 1300) in the cavity (302, 1200).

17. A medical fixation device (001, 1001) according to claim 1, wherein the first elongate element (100, 1100), the second elongate element (200, 1200), the base element (300, 1300), and the connection between the first elongate element (100) and the second elongate element (200) are configured such that, when fixed to the operating table (502) and when forces of 90N, in particular horizontal or vertical transversal forces, are exerted on the first elongate element (100, 1100), the displacement of the first elongate element (100, 1100) relative to the operating table (502) is less than 10 mm, preferably less than 7 mm, more preferably less than 5 mm.

18. A medical fixation device (001, 1001) according to claim 1, further comprising a connection part (400, 1400) for connecting an end of the first elongate element to an end of the second elongate element, wherein the first elongate element (100, 1100) and the connection part (400, 1400) are configured to allow rotatable connection of the first elongate element relative to at least a part of the connection part (400, 1400);

wherein the first elongate element (100, 1100) and the connection part (400, 1400) are further configured to allow secure fixation of the first elongate element to the connection part (400, 1400) in at least one fixed angular position of the first elongate element (100, 1100) relative to the second elongate element (200, 1200);

wherein the medical fixation device further comprises a fixation mechanism configured (406, 1450) configured for the secure fixation of the first elongate element (100, 1100) to the connection part (400, 1400) by connecting the fixation mechanism (406, 1450) to the first elongate element and the connection part, and wherein the first elongate element (100, 1100) can only rotate with respect to connection part (400, 1400) when the fixation mechanism configured (406, 1450) for secure fixation is not connected to the first elongate element.

19. A method for installation of the medical fixation device (001, 1001) of claim 1, the method comprising the steps of:

connecting the base element (300, 1300) to the side of the operating table (502);

securely fixing the base element (300, 1300) to the side of the operating table (502);

unfolding the medical fixation device (001, 1001) to the desired position of the first elongate element (100, 1100) in the space around the operating table (503).

20. A medical fixation device (001, 1001) for connecting one or more surgical instruments (600) such as retractor devices (500) to an operating table (502) in the space (503) around the operating table, the medical device comprising:

two elongate elements, a first elongate element (100, 1100) and a second elongate element (200, 1200), wherein an end of the first elongate element is connected to an end of the second elongate element, a fixation mechanism configured (406, 1450) for secure fixation of the first elongate element (100, 1100) in at least one fixed angular position relative to the second elongate element (200, 1200), a base element (300, 1300) connected to the second elongate element (200, 1200) and configured to be connected to the operating table (502), one or more first screws (305, 1305) for secure fixation of the second elongate element (200, 1200) to the base element (300, 1300), and one or more second screws (303, 1303) for secure fixation of the base element (300, 1300) to the operating table (502), wherein the first elongate element (100, 1100) is configured to be releasably connected to one or more, preferably two or more, more preferably three or more, surgical instruments (600), and wherein the connection between the first elongate element (100, 1100) and the second elongate element (200, 1200) is configured to allow rotatable connection of the first elongate element (100, 1100) relative to the second elongate element (200, 1200) when the fixation mechanism configured (406, 1450) for secure fixation of the first elongate element (100, 1100) in the at least one fixed angular position relative to the second elongate element (200, 1200) is not connected.

* * * * *